US010457988B2

(12) United States Patent
Keller et al.

(10) Patent No.: US 10,457,988 B2
(45) Date of Patent: *Oct. 29, 2019

(54) MIRNAS AS DIAGNOSTIC MARKERS

(71) Applicants: Siemens Aktiengesellschaft, München (DE); Siemens Healthcare Diagnostics Holding GmbH, Eschborn (DE)

(72) Inventors: Andreas Keller, Püttlingen (DE); Cord Friedrich Stähler, Hirschberg an der Bergstraße (DE); Christina Backes, Saarbrücken (DE); Eckart Meese, Hütschenhausen (DE); Petra Leidinger, Wadern (DE); Andreas Kappel, Glashütten (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/442,858

(22) PCT Filed: Nov. 4, 2013

(86) PCT No.: PCT/EP2013/072920
§ 371 (c)(1),
(2) Date: May 14, 2015

(87) PCT Pub. No.: WO2014/075939
PCT Pub. Date: May 22, 2014

(65) Prior Publication Data
US 2015/0292013 A1 Oct. 15, 2015

(30) Foreign Application Priority Data

Nov. 16, 2012 (EP) .................................. 12192979

(51) Int. Cl.
*C12Q 1/6883* (2018.01)
*A61K 31/7105* (2006.01)
*A61K 31/712* (2006.01)

(52) U.S. Cl.
CPC ........ *C12Q 1/6883* (2013.01); *A61K 31/7105* (2013.01); *C12Q 2600/112* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| 7,687,616 | B1* | 3/2010 | Bentwich | C12Q 1/6883 536/23.1 |
| 9,493,832 | B2* | 11/2016 | Vilanova | C12Q 1/6883 |
| 2003/0013649 | A1* | 1/2003 | Rosen | C07K 14/47 435/69.1 |
| 2007/0083334 | A1* | 4/2007 | Mintz | G06F 19/24 702/19 |
| 2009/0081640 | A1 | 3/2009 | Umansky et al. | |
| 2010/0234445 | A1 | 9/2010 | Lui et al. | |
| 2010/0280099 | A1* | 11/2010 | Elmen | C12N 15/111 514/44 A |
| 2015/0197805 | A1 | 7/2015 | Umansky et al. | |

FOREIGN PATENT DOCUMENTS

| CN | 101861399 A | 10/2010 |
| EP | 2077326 A1 | 7/2009 |
| EP | 2112235 A1 | 10/2009 |
| WO | WO-2009/009457 A1 | 1/2009 |
| WO | WO-2009/025852 A2 | 2/2009 |
| WO | WO-2009/036236 A1 | 3/2009 |
| WO | WO-2011/057003 A2 | 5/2011 |
| WO | WO-2012/036433 A2 | 3/2012 |
| WO | WO-2012/145363 A1 | 10/2012 |
| WO | WO-2013/065819 A1 | 5/2013 |
| WO | WO-2013/072920 A2 | 5/2013 |
| WO | WO-2014/075911 A1 | 5/2014 |

OTHER PUBLICATIONS

Schulz, et al. (2002) Neuroscience Letters, v.326:37-40.*
NCBI RefSeq NG_029781.1 [online]. [retrived on Jun. 7, 2016]. Retrieved from the Internet: <http://www.ncbi.nlm.nih.gov/nuccore/343887354/>.*
Strimbu, et al. "What are Biomarkers?" Nov. 2010, Curr. Opin. HIV AIDS, v.5(6):463-6. (Year: 2010).*
Biomarkers Definitions Working Group "Biomarkers and surrogate endpoints: Preferred definitions and conceptual framework." Mar. 2001, Clinical Pharmacology & Therapeutics, v.69:89-95. (Year: 2001).*
Leidinger, et al. (2013) "A blood based 12-miRNA signature of Alzheimer disease patients." Genome Biology, vol. 14:R78 (16 pages). (Year: 2013).*
Office Action dated Apr. 26, 2016 issued in U.S. Appl. No. 14/442,756.
Barbato, C., et al. (2009), "Searching for MIND: MicroRNAs in Neurodegenerative Diseases", *Journal of Biomedicine and Biotechnology*, 14(1): 8 pages.
De Smaele, et al. (2010), "MicroRNAs as biomarkers for CNS cancer and other disorders", *Brain Res.* 1138: 100-111.
European Search Report dated Aug. 2, 2013 issued in European Patent Application No. 012192974.9.
European Search Report dated Aug. 21, 2013 issued in European Patent Application No. 12192979.8.
European Search Report dated May 3, 2013 issued in European Patent Application No. 12192979.8.
FASTX-Toolkit; http://hannonlab.cshl.edu/fastx_toolkit/; retrieved on Nov. 19, 2012, 10:16 a.m.
Hudson, G., et al. (2012), "No consistent evidence for association between mtDNA variants and Alzheimer disease", *Neurology*, 78: 1038-1042.

(Continued)

*Primary Examiner* — Jennifer Pitrak McDonald
(74) *Attorney, Agent, or Firm* — Harness Dickey & Pierce P.L.C.

(57) ABSTRACT

The invention relates to novel miRNA markers useful for diagnosis or therapy of disease, in particular for neuronal disorders such as Alzheimer's Disease (AD).

1 Claim, 2 Drawing Sheets
Specification includes a Sequence Listing.

(56) References Cited

OTHER PUBLICATIONS

International Search Report and Written Opinion dated Dec. 3, 2013 issued in PCT Patent Application No. PCT/EP2013/065819.
International Search Report and Written Opinion dated Mar. 7, 2014 issued in PCT Patent Application No. PCT/EP2013/072567.
Keller, A., et al. (2011), "Toward the blood-borne miRNome of human diseases", *Nature Methods*, 8(10): 841-843.
Lange, J., et al. (2010), miRNA biomarkers from blood—A promising approach for minimally invasive diagnostic testing, *Gerburtshilfe Und Frauenheilkunde*, 70(2): 137-141—English Abstract Only.
Maes, O., et al. (2009), "MicroRNA: Implications for Alzheimer Disease and other Human CNS Disorders", *Current Genomics*, 10: 154-168.
Malaplate-Armand, C., et al. (2009), "Diagnostic biologique de la maladie d'Alzheimer: avancées, limites et perspectives, Biomarkers for early diagnosis of Alzheimer's disease: Current update and future directions", *Revue Neurologique*, 165: 511-520—English Abstract Only.
Margis, R., et al. (2011), "Identification of blood microRNAs associated to Parkinsonis disease", *Journal of Biotechnology*, 152: 96-101.
Satoh, J. (2010), "MircoRNAs and Their Therapeutic Potential for Human Diseases: Aberrant MicroRNA Expression in Alzheimer's Disease Brains", *J. Pharmacol Sci.* 114: 269-275.
Schipper, H., et al. (2007), "MicroRNA Expression in Alzheimer Blood Mononuclear Cells", *Gene Regulation and Systems Biology*, 1: 263-274.
TAM tool; http://202.38.126.151/hmdd/tools/tam.html; retrieved on Nov. 19, 2012, 10:14 a.m.
Geekiyanage, H., et al. (2012), "Blood serum miRNA: Non-invasive biomarkers for Alzheimer's disease", *Exp Neurol.* 235(2): 491-496.
International Search Report and Written Opinion dated Mar. 7, 2014 issued in PCT Patent Application No. PCT/EP2013/072920.
Chinese Office Action dated May 27, 2016 in corresponding Chinese Patent Application CN 201380068818.0—English translation.
Friedländer, M., et al. (2012), "miRDeep2 accurately identifies known and hundreds of novel microRNA genes in seven animal clades", Nucleic Acids Research, 40(1): 37-52.
Office Action dated Aug. 29, 2016 issued in U.S. Appl. No. 14/442,756.
Kim et al. (2007), "A microRNA Feedback Circuit in Midbrain Dopamine Neurons", Science; 317(5842): pp. 1220-1224.
Martins et al. (2011), "Convergence of miRNA Expression Profiling, Alpha-Synuclein Interacton and GWAS in Parkinson's Disease", PLoS One, vol. 6, Iss 10; e25443; pp. 1-11.
Office Action dated Apr. 19, 2016 issued in co-pending Chinese Patent Application No. 2013/80069445.9.
Office Action dated Sep. 8, 2017 issued in U.S. Appl. No. 14/442,439.
Office Action dated Mar. 19, 2018 issued in U.S. Appl. No. 14/442,439.
Office Action dated Apr. 10, 2017 issued in U.S. Appl. No. 14/442,756.
Office Action dated Oct. 23, 2017 issued in U.S. Appl. No. 14/442,756.
Office Action dated Mar. 7, 2017 issued in U.S. Appl. No. 14/442,439.
U.S. Appl. No. 14/442,756, filed May 14, 2015.
U.S. Appl. No. 14/442,439, filed May 13, 2015.

* cited by examiner

MIRNAS AS DIAGNOSTIC MARKERS

PRIORITY STATEMENT

This application is a national phase application under 35 U.S.C. § 371 of PCT International Application No. PCT/EP2013/072920 which has an International filing date of 4 Nov. 2013, which designated the United States of America, and which claims priority to European patent application number 12192979.8 filed 16 Nov. 2012. The entire contents of each patent application referenced above are hereby incorporated by reference.

REFERENCE TO A SEQUENCE LISTING

This application contains references to amino acid sequences and/or nucleic acid sequences which have been submitted concurrently herewith as the sequence listing text file 61494576_1.TXT file size 52.7 KiloBytes (KB), created on 11 Nov. 2013. The aforementioned sequence listing is hereby incorporated by reference in its entirety pursuant to 37 C.F.R. § 1.52(e)(5).

FIELD OF THE INVENTION

The invention relates to novel miRNA markers and their uses. In particular, the invention relates to novel miRNA markers useful for diagnosis or therapy of disease, in particular for neuronal disorders such as Alzheimer's Disease (AD).

BACKGROUND OF THE INVENTION

Very recently, molecular diagnostics has increasingly gained in importance. It has found an entry into the clinical diagnosis of diseases (inter alia detection of infectious pathogens, detection of mutations of the genome, detection of diseased cells and identification of risk factors for predisposition to a disease).

In particular, through the determination of gene expression in tissues, nucleic acid analysis opens up very promising new possibilities in the study and diagnosis of disease.

Nucleic acids of interest to be detected include genomic DNA, expressed mRNA and other RNAs such as MicroRNAs (abbreviated miRNAs). MiRNAs are a new class of small RNAs with various biological functions (A. Keller et al., Nat Methods. 2011 8(10):841-3). They are short (average of 20-24 nucleotide) ribonucleic acid (RNA) molecules found in eukaryotic cells. Several hundred different species of microRNAs (i.e. several hundred different sequences) have been identified in mammals. They are important for post-transcriptional gene-regulation and bind to complementary sequences on target messenger RNA transcripts (mRNAs), which can lead to translational repression or target degradation and gene silencing. As such they can also be used as biologic markers for research, diagnosis and therapy purposes.

OBJECT OF THE INVENTION

The technical problem underlying the present invention is to provide new biological markers and uses thereof.

SUMMARY OF THE INVENTION

Before the invention is described in detail, it is to be understood that this invention is not limited to the particular component parts of the process steps of the methods described as such methods may vary. It is also to be understood that the terminology used herein is for purposes of describing particular embodiments only, and is not intended to be limiting. It must be noted that, as used in the specification and the appended claims, the singular forms "a," "an" and "the" include singular and/or plural referents unless the context clearly dictates otherwise. It is also to be understood that plural forms include singular and/or plural referents unless the context clearly dictates otherwise. It is moreover to be understood that, in case parameter ranges are given which are delimited by numeric values, the ranges are deemed to include these limitation values.

In one aspect, the invention provides an isolated nucleic acid molecule comprising
(a) a nucleotide sequence selected from the group of nucleotide sequences having a sequence according to SEQ ID NO 2, SEQ ID NO 1, and SEQ ID NO 3 to SEQ ID NO 365,
(b) a nucleotide sequence which is the complement thereof, or
(c) a nucleotide sequence which has an identity of at least 90% to a sequence of (a) or (b).

The invention further provides the use of at least one nucleic acid molecule of the invention for evaluating physiological and/or pathological condition of a subject.

DETAILED DESCRIPTION OF THE INVENTION

Definitions

Figure 1:
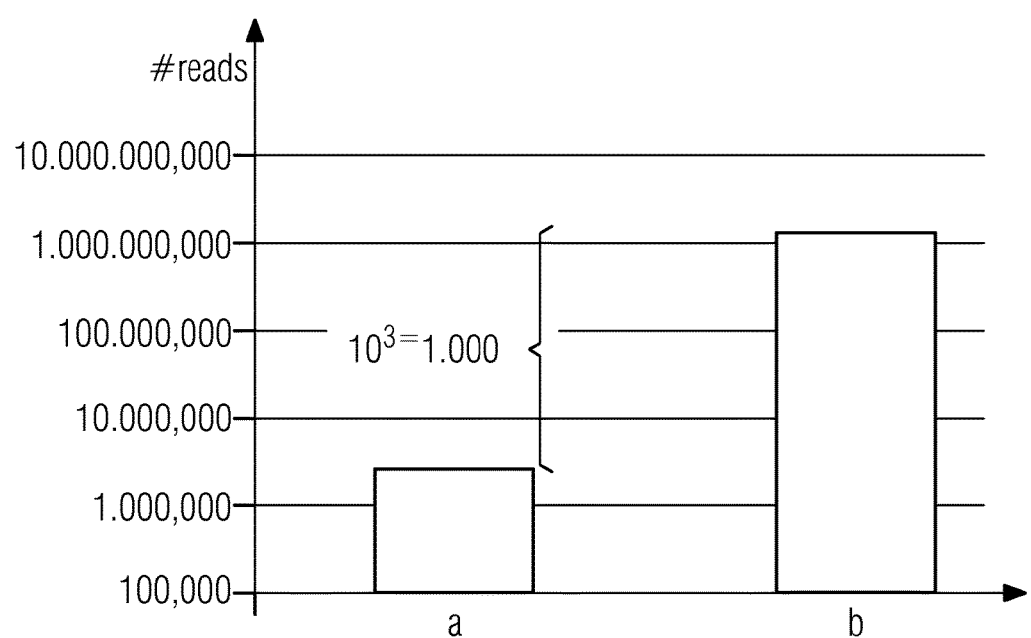
FIG. 1 shows the distribution of (a) novel nucleic acid molecule miRNA markers of the invention vs. (b) known miRNA markers in blood.

Unless defined otherwise, technical and scientific terms used herein have the same meaning as commonly understood by one of ordinary skill in the art to which this invention belongs.

The term "nucleic acid molecule" refers to a polynucleotide molecule having a defined sequence. It comprises DNA molecules, RNA molecules, nucleotide analog molecules and combinations thereof, such as DNA molecules or RNA molecules with incorporated nucleotide analogs.

The term "marker" or "biomarker" refers to a biological molecule, e.g., a nucleic acid, peptide, protein, hormone, etc., whose presence or concentration can be detected and correlated with a known condition, such as a disease state, or with a clinical outcome, such as response to a treatment.

The term "evaluating the physiological and/or pathological condition" comprises classifying a sample of a patient suffering from or at risk of developing a pathological condition, screening for the presence or risk of developing a pathological condition, predicting a risk of developing the pathological condition, or predicting an outcome of the pathological condition in a patient suffering from or at risk of developing pathological condition.

The term "predicting an outcome" of a pathological condition or of disease, as used herein, is meant to include both a prediction of an outcome of a patient undergoing a given therapy and a prognosis of a patient who is not treated.

An "outcome" within the meaning of the present invention is a defined condition attained in the course of the disease. This disease outcome may e.g. be a clinical condition such as "relapse of disease", "remission of disease", "response to therapy", a disease stage or grade or the like.

A "risk" is understood to be a probability of a subject or a patient to develop or arrive at a certain disease outcome. The term "risk" in the context of the present invention is not meant to carry any positive or negative connotation with regard to a patient's wellbeing but merely refers to a probability or likelihood of an occurrence or development of a given event or condition.

The term "clinical data" relates to the entirety of available data and information concerning the health status of a patient including, but not limited to, age, sex, weight, menopausal/hormonal status, etiopathology data, anamnesis data, data obtained by in vitro diagnostic methods such as blood or urine tests, data obtained by imaging methods, such as x-ray, computed tomography, MRI, PET, spect, ultrasound, electrophysiological data, genetic analysis, gene expression analysis, biopsy evaluation, intraoperative findings.

The term "classification of a sample" of a patient, as used herein, relates to the association of said sample with at least one of at least two categories. These categories may be for example "high risk" and "low risk", high, intermediate and low risk, wherein risk is the probability of a certain event occurring in a certain time period, e.g. occurrence of disease, progression of disease, etc. It can further mean a category of favourable or unfavourable clinical outcome of disease, responsiveness or non-responsiveness to a given treatment or the like. Classification may be performed by use of an algorithm, in particular a discriminate function. A simple example of an algorithm is classification according to a first quantitative parameter, e.g. expression level of a nucleic acid of interest, being above or below a certain threshold value. Classification of a sample of a patient may be used to predict an outcome of disease or the risk of developing a disease. Instead of using the expression level of a single nucleic acid of interest, a combined score of several nucleic acids of interest of interest may be used. Further, additional data may be used in combination with the first quantitative parameter. Such additional data may be clinical data from the patient, such as sex, age, weight of the patient, disease grading etc.

A "discriminant function" is a function of a set of variables used to classify an object or event. A discriminant function thus allows classification of a patient, sample or event into a category or a plurality of categories according to data or parameters available from said patient, sample or event. Such classification is a standard instrument of statistical analysis well known to the skilled person. E.g. a patient may be classified as "high risk" or "low risk", "in need of treatment" or "not in need of treatment" or other categories according to data obtained from said patient, sample or event. Classification is not limited to "high vs. low", but may be performed into a plurality of categories, grading or the like. Examples for discriminant functions which allow a classification include, but are not limited to discriminant functions defined by support vector machines (SVM), k-nearest neighbors (kNN), (naive) Bayes models, or piecewise defined functions such as, for example, in subgroup discovery, in decision trees, in logical analysis of data (LAD) an the like.

The term "expression level" refers, e.g., to a determined level of expression of a nucleic acid of interest. The term "pattern of expression levels" refers to a determined level of expression com-pared either to a reference nucleic acid, e.g. from a control, or to a computed average expression value, e.g. in DNA-chip analyses. A pattern is not limited to the comparison of two genes but is also related to multiple comparisons of genes to reference genes or samples. A certain "pattern of expression levels" may also result and be determined by comparison and measurement of several nucleic acids of interest disclosed hereafter and display the relative abundance of these transcripts to each other. Expression levels may also be assessed relative to expression in different tissues, patients versus healthy controls, etc.

A "reference pattern of expression levels", within the meaning of the invention shall be understood as being any pattern of expression levels that can be used for the comparison to another pattern of expression levels. In a preferred embodiment of the invention, a reference pattern of expression levels is, e.g., an average pattern of expression levels observed in a group of healthy or diseased individuals, serving as a reference group.

In The context of the present invention a "sample" or a "biological sample" is a sample which is derived from or has been in contact with a biological organism. Examples for biological samples are: cells, tissue, body fluids, biopsy specimens, blood, urine, saliva, sputum, plasma, serum, cell culture supernatant, and others.

A "probe" is a molecule or substance capable of specifically binding or interacting with a specific biological molecule. The term "primer", "primer pair" or "probe", shall have ordinary meaning of these terms which is known to the person skilled in the art of molecular biology. In a preferred embodiment of the invention "primer", "primer pair" and "probes" refer to oligonucleotide or polynucleotide molecules with a sequence identical to, complementary too, homologues of, or homologous to regions of the target molecule or target sequence which is to be detected or quantified, such that the primer, primer pair or probe can specifically bind to the target molecule, e.g. target nucleic acid, RNA, DNA, cDNA, gene, transcript, peptide, polypeptide, or protein to be detected or quantified. As understood herein, a primer may in itself function as a probe. A "probe" as understood herein may also comprise e.g. a combination of primer pair and internal labeled probe, as is common in many commercially available qPCR methods.

A "miRNA" is a short, naturally occurring RNA molecule and shall have the ordinary meaning understood by a person skilled in the art. A "molecule derived from an miRNA" is a molecule which is chemically or enzymatically obtained from an miRNA template, such as cDNA.

The term "array" refers to an arrangement of addressable locations on a device, e.g. a chip device. The number of locations can range from several to at least hundreds or thousands. Each location represents an independent reaction site. Arrays include, but are not limited to nucleic acid arrays, protein arrays and antibody-arrays. A "nucleic acid array" refers to an array containing nucleic acid probes, such as oligonucleotides, polynucleotides or larger portions of genes. The nucleic acid on the array is preferably single stranded. A "microarray" refers to a biochip or biological chip, i.e. an array of regions having a density of discrete regions with immobilized probes of at least about 100/cm2.

A "PCR-based method" refers to methods comprising a polymerase chain reaction PCR. This is a method of exponentially amplifying nucleic acids, e.g. DNA or RNA by enzymatic replication in vitro using one, two or more primers. For RNA amplification, a reverse transcription may be used as a first step. PCR-based methods comprise kinetic or quantitative PCR (qPCR) which is particularly suited for the analysis of expression levels). When it comes to the determination of expression levels, a PCR based method may for example be used to detect the presence of a given mRNA by (1) reverse transcription of the complete mRNA pool (the so called transcriptome) into cDNA with help of a reverse transcriptase enzyme, and (2) detecting the presence of a given cDNA with help of respective primers. This approach is commonly known as reverse transcriptase PCR (rtPCR). The term "PCR based method" comprises both end-point PCR applications as well as kinetic/real time PCR techniques applying special fluorophors or intercalating dyes which emit fluorescent signals as a function of amplified target and allow monitoring and quantification of the target. Quantification methods could be either absolute by external standard curves or relative to a comparative internal standard.

The term "next generation sequencing" or "high throughput sequencing" refers to high-throughput sequencing technologies that parallelize the sequencing process, producing thousands or millions of sequences at once. Examples include Massively Parallel Signature Sequencing (MPSS) Polony sequencing, 454 pyrosequencing, Illumina (Solexa) sequencing, SOLiD sequencing, Ion semiconductor sequencing, DNA nanoball sequencing, Helioscope™ single molecule sequencing, Single Molecule SMRT™ sequencing, Single Molecule real time (RNAP) sequencing, Nanopore DNA sequencing.

In one aspect, the invention provides an isolated nucleic acid molecule comprising
(a) a nucleotide sequence selected from the group of nucleotide sequences having a sequence according to SEQ ID NO 2, SEQ ID NO 1, and SEQ ID NO 3 to SEQ ID NO 365,
(b) a nucleotide sequence which is the complement thereof, or
(c) a nucleotide sequence which has an identity of at least 90% to a sequence of (a) or (b).

According to an aspect of the invention, the nucleic acid molecule is selected from the group of RNA, DNA or nucleic acid analog molecules.

According to an aspect of the invention, the nucleic acid molecule comprises at least one modified nucleotide analog.

According to an aspect of the invention, the nucleic acid molecule is an expression vector.

The invention further provides the use of at least one nucleic acid molecule of the invention for evaluating physiological and/or pathological condition of a subject.

According to an aspect of the invention the use can further comprise the step of determining in said sample of said subject an expression level of said nucleic acid molecule.

According to an aspect of the invention the sample can be a blood sample.

According to an aspect of the invention evaluating the physiological and/or pathological condition comprises classifying a sample of a patient suffering from or at risk of developing a pathological condition, predicting a risk of developing the pathological condition, or predicting an outcome of the pathological condition in a patient suffering from or at risk of developing pathological condition.

According to an aspect of the invention the use can further comprise the steps of comparing an expression level or a pattern of expression levels(s) with one or several reference pattern(s) of expression levels and evaluating the physiological and/or pathological condition from the outcome of the comparison.

The invention further provides a pharmaceutical composition containing of at least one nucleic acid molecule of the invention.

The invention further provides the use of the composition of the invention for diagnostic and/or therapeutic applications. For example, miRNAs may be detected in biological samples, e. g. in tissue sections, blood samples, serum samples or other, in order to determine and classify certain cell types or tissue types or miRNA-associated pathogenic disorders which are characterized by differential expression of miRNA-molecules or miRNA-molecule patterns. Further, the developmental stage of cells may be classified by determining temporarily expressed miRNA molecules.

Further, the claimed nucleic acid molecules are suitable for therapeutic applications. For example, the nucleic acid molecules may be used as modulators or targets of developmental processes or disorders associated with developmental dysfunctions, such as cancer metabolic diseases, degenerative diseases etc.

In general, the claimed nucleic acid molecules may be used as a modulator of the expression of genes which are at least partially complementary to said nucleic acid. Further, miRNA molecules may act as target for therapeutic screening procedures, e. g. inhibition or activation of miRNA molecules might modulate a cellular differentiation process, e. g. apoptosis.

The invention further provides a kit comprising means for determining the presence and/or amount of an expression level of at least one nucleic acid molecule of the invention.

EXAMPLES

Additional details, features, characteristics and advantages of the object of the invention are further disclosed in the following description and figures of the respective examples, which, in an exemplary fashion, show preferred embodiments of the present invention. However, these examples should by no means be understood as to limit the scope of the invention.

The invention provides very rare variants of miRNAs that are present in blood cells. The abundance of miRNAs in samples of Alzheimer's Disease patients and patients suffering from other neuronal disorders has been compared in an unbiased approach against healthy controls. This approach involved a massive effort of sequencing miRNAs from samples and thus was open to the discovery of novel markers not yet described in the prior art.

Materials and Methods
Patient Cohorts

The expression of miRNAs in peripheral blood of a total of 219 patients and healthy controls was determined, either by NGS or by qRT-PCR or both. Blood was obtained from patients with Alzheimer's Disease (AD) (n=106), patients with Mild Cognitive Impairment (MCI) (n=21), patients with Multiple Sclerosis (Clinically Isolated Syndrome, CIS) (n=17), patients with Parkinson's Disease (PD) (n=9), patients with Mild Depression (DEP) (n=15), Bipolar Disorder (BD) (n=15), and from healthy controls (n=22).

First, samples from AD patients (n=48), MCI patients (n=20) and healthy controls (n=22) were analyzed by Next-generation sequencing. For validation purposes the expression of single miRNAs was analyzed using qRT-PCR in the same samples as used for NGS, if enough RNA was available. The number of samples was further expanded by further samples from patients with AD, CIS, PD, DEP, BD, and Schiz, resulting in a total of 205 samples analyzed by qRT-PCR. In detail, a total of 95 samples from AD patients, 19 samples from MCI patients, 17 samples from CIS patients, 9 samples from PD patients, 15 samples from DEP patients, 15 samples from BD patients, 14 samples from Schiz patients, and 21 samples from healthy controls were analyzed.

RNA Isolation

Total RNA including miRNA was isolated using the PAXgene Blood miRNA Kit (Qiagen) following the manufacturer's recommendations. Isolated RNA was stored at −80° C. RNA integrity was analyzed using Bioanalyzer 2100 (Agilent) and concentration and purity were measured using NanoDrop 2000 (Thermo Scientific). A total of four samples (three controls and one RRMS) failed the quality criteria and were excluded from the study.

Library Preparation and Next-Generation Sequencing

For the library preparation, 200 ng of total RNA was used per sample, as determined with a RNA 6000 Nano Chip on the Bioanalyzer 2100 (Agilent). Preparation was performed following the protocol of the TruSeq Small RNA Sample Prep Kit (Illumina). Concentration of the ready prepped libraries was measured on the Bioanalyzer using the DNA 1000 Chip. Libraries were then pooled in batches of six samples in equal amounts and clustered with a concentration of 9 pmol in one lane each of a single read flowcell using the cBot (Illumina). Sequencing of 50 cycles was performed on a HiSeq 2000 (Illumina). Demultiplexing of the raw sequencing data and generation of the fastq files was done using CASAVA v.1.8.2.

NGS Data Analysis

The raw illumina reads were first preprocessed by cutting the 3' adapter sequence using the program fastx_clipper from the FASTX-Toolkit (http://hannonlab.cshl.edu/fastx_toolkit/). Reads shorter than 18 nts after clipping were removed. The remaining reads are reduced to unique reads and their frequency per sample to make the mapping steps more time efficient. For the remaining steps, we used the miRDeep2 pipeline. These steps consist of mapping the reads against the genome (hg19), mapping the reads against miRNA precursor sequences from mirbase release v18, summarizing the counts for the samples, and the prediction of novel miRNAs. Since the miRDeep2 pipeline predicts novel miRNAs per sample, the miRNAs were merged afterwards as follows: first, the novel miRNAs per sample that have a signal-to-noise ratio of more than 10 were extracted. Subsequently, only those novel miRNAs that are located on the same chromosome were merged, and both their mature forms share an overlap of at least 11 nucleotides.

Bioinformatics Analysis

First the read counts were normalized using standard quantile normalization. All miRNAs with less than 50 read counts were excluded from further considerations. Next, we calculated for each miRNA the area under the receiver operator characteristic curve (AUC), the fold-change, and the significance value (p-value) using t-tests. All significance values were adjusted for multiple testing using the Benjamini Hochberg approach. The bioinformatics analyses have been carried out using the freely available tool. R. Furthermore, we carried out a miRNA enrichment analysis using the TAM tool (http://202.38.126.151/hmdd/tools/tam.html).

Results

Screening Using High-Throughput Sequencing

The invention provides very rare variants of miRNAs that are present in blood cells. While common variants have already been discovered and are heavily overlapping with miRNAs discovered from tissue biopsies, a substantial part of miRNAs is expected to be still unknown. Herein, patients suffering neurological disorders including mild cognitive impairment, Alzheimer's disease or multiple sclerosis as well as unaffected controls were characterized. About 2 billion sequences from the patient and control samples were generated, of which around 1.4 billion matched to known or predicted novel miRNAs. As detailed in FIG. 1, the vast majority of these sequences matched known miRNAs (99.9%) while only around 0.1% matched to predicted novel miRNAs, pointing out why the enormous sequencing capacity had to be used. It has been found that these novel miRNAs can be used as diagnostic markers indicative of disease conditions such as neuronal diseases, e.g. Alzheimer's Disease.

The most abundant miRNAs were hsa-miR-486-5p with an average read-count of Ser. No. 13/886,676 and a total of 1.2 billion reads mapping to this miRNA, hsa-miR-92a-3p with an average of 575,359 reads and a total of 52 million reads mapping to this miRNA and miR-451a with an average of 135,012 reads and a total of 12 million reads mapping to this miRNA.

Additionally, 365 novel mature miRNA candidates were detected that have been previously not present in the Sanger miRBase. These miRNA candidates have generally however been much less abundant as compared to the known human miRNAs. The most abundant one, denoted as brain-miR-314 was detected on average with 3,587 reads per sample and a total of 322,868 reads. Second highest expressed miRNA, brain-miR-247 was present on average with 3,112 and with a total of 280,115 reads, third most abundant miRNA brain-miR-12 at an average of 2,630 and a total of 236,728 reads. In the list of all, novel and known miRNAs, brain-miR-314 would be ranked on position 37, i.e., 36 known human miRNAs were more abundant than the highest abundant novel one. While a total of 1.4 Bn reads mapped to the known miRNAs, only 2.3 Mn mapped to the novel miRNA candidates. This relation shows that a very high sequencing capacity is required to reach the sensitivity in order to detect rare variants of novel miRNAs in human blood samples.

In FIG. 1 the bar diagram shows on a logarithmic scale the distribution of around 1.4 billion reads to novel—as well as known miRNAs. As the diagram outlines, roughly 99.9% belong to known miRNAs, underlining that a) the selection of the right biological source, namely blood cells, and b) the ultra high sensitivity have been key to discover the novel markers.

It is noted that the mature miRNa originate from miRNA precursor molecules of length of around 120 bases. Several examples exists where the miRNA precursors vary from each other while the subset of the around 20 bases belonging to the mature miRNA are identical. Thus, novel mature miRNAs can have the same sequence but different SEQ ID NO identifiers.

TABLE 1

Novel miRNA markers

| SEQ ID NO | miRNA | sequence | readcount |
|---|---|---|---|
| 1 | brain-mir-314 | ACUCCCACUGCUUCACUUGAUUAG | 349075 |
| 2 | brain-mir-247 | ACGCCCACUGCUUCACUUGACUAG | 301937 |
| 3 | brain-mir-12 | ACUCCCACUGCUUGACUUGACUAG | 254654 |
| 4 | brain-mir-256 | GGAAUACCGGGUGCUGUAGGCUU | 233887 |
| 5 | brain-mir-278 | UGCCUGUCUGAGCGUCGCU | 165451 |
| 6 | brain-mir-342 | UCGAAUCCCAUCCUCGUCGCU | 155546 |
| 7 | brain-mir-111 | CACUGCUAAAUUUGGCUGGCUU | 123961 |
| 8 | brain-mir-250 | AUAACGGGUGCUGUAGGCUU | 88815 |
| 9 | brain-mir-114 | CACUGCAACCUCUGCCUCCGGU | 74782 |
| 10 | brain-mir-370 | GGCUGGUCUGAUGGUAGUGGGUUA | 62219 |
| 11 | brain-mir-397 | ACUGCUAAAUUUGACUAGCUA | 48159 |
| 12 | brain-mir-158 | UUUCGAUGGUAGUCGCCGUGCC | 46289 |
| 13 | brain-mir-311 | CACUGCAACCUCUGCCUCCCGA | 32163 |
| 14 | brain-mir-138 | CCUCACCAUCCCUUCUGCCUGCA | 16928 |
| 15 | brain-mir-159 | UUUCCUCUGCUCUCAUACCACA | 16474 |
| 16 | brain-mir-143 | CCUCACCACCCUUCUGCCUGCA | 16355 |
| 17 | brain-mir-110 | UCACCACCCCUUCUGCCUGCA | 16317 |
| 18 | brain-mir-249 | CACUGCAACCUCUGCCUCCUG | 15824 |
| 19 | brain-mir-83 | CAGGGUCUCGUUCUGUUGCC | 15659 |
| 20 | brain-mir-246 | CACUGCUACCUCUGCCUCCGG | 14440 |
| 21 | brain-mir-77 | UCUGGGCAUCAAAGUGAGACC | 14348 |
| 22 | brain-mir-270 | UCUGGGCAACAGAGUGAGACC | 13951 |
| 23 | brain-mir-321 | UCUGGGCAACAAAGUGAUACC | 13783 |
| 24 | brain-mir-241 | UCUGGGCAACAAGGUGAGACC | 13769 |
| 25 | brain-mir-262 | CUGAGAAGACAGUCGAACUUGACU | 13550 |
| 26 | brain-mir-209* | GUCUACGACCAUACCACCC | 10834 |
| 27 | brain-mir-184 | UCAAAUCCCGGACGAGCCC | 10051 |
| 28 | brain-mir-313 | AGUCUUGCUCUGUCGCCCAGG | 8955 |
| 29 | brain-mir-122 | GCGGCGGCGGCGGCGGCGGCGGCGG | 8929 |
| 30 | brain-mir-101* | AAGGUAGAUAGAACAGGUCU | 8469 |
| 31 | brain-mir-48 | CUUCCCCACCCUCUCCUGCAGC | 7734 |
| 32 | brain-mir-9 | UCAGGCUCCGUCCCCUCCCU | 7513 |
| 33 | brain-mir-186 | CCACCCUGAACGCGCCCG | 6858 |
| 34 | brain-mir-13 | CGGCGGCGGCGGCGGCGGCGGC | 6589 |
| 35 | brain-mir-232 | UUGCUCUGCUCUCCCUUGUACU | 6436 |
| 36 | brain-mir-209 | CUGGUUAGUACUUGGAUGGG | 6284 |
| 37 | brain-mir-186* | GGUUAGUACUUGGAUGGGA | 5136 |
| 38 | brain-mir-220 | UCCGGAUCCGGCUCCGCGCCU | 4710 |

TABLE 1-continued

Novel miRNA markers

| SEQ ID NO | miRNA | sequence | readcount |
|---|---|---|---|
| 39 | brain-mir-124 | GCGGCGGCGGCGGCGGCGGCGGAGG | 4668 |
| 40 | brain-mir-93 | AGUCUUGCUCUGUCGCCCCGG | 4436 |
| 41 | brain-mir-20 | UCGACUCCUGGCUGGCUCG | 4397 |
| 42 | brain-mir-433 | GCGGCGGCGGCGGCGGCGGCGG | 4393 |
| 43 | brain-mir-108 | UAUGUCCCACCCCCACUCCUGU | 4147 |
| 44 | brain-mir-102* | UCUGAUCGUUCCCCUCCGUACAG | 4102 |
| 45 | brain-mir-255 | AGUCUUGCUCUGUUGCCCAGG | 3998 |
| 46 | brain-mir-102 | UAUGGAGGUCUCUGUCUGGCU | 3996 |
| 47 | brain-mir-298 | AGUCUUGCUCUGUCGCCCGGG | 3952 |
| 48 | brain-mir-11 | UCAGGCUCAGUCCCCUCCAU | 3948 |
| 49 | brain-mir-296 | AGUCUUGCUCUGUCACCCAGG | 3939 |
| 50 | brain-mir-28 | AGUCUUGCUGUGUCGCCCAGG | 3879 |
| 51 | brain-mir-116 | AGCCCGUCGGACCUCCGCCAUGC | 3720 |
| 52 | brain-mir-315 | GCGGCGGCGGCGGCGGCGGCGCGGG | 3474 |
| 53 | brain-mir-398 | GGCUGGUCCGAGUGCAGUGGUGUU | 3334 |
| 54 | brain-mir-200 | UUCCUGGCUCUCUGUUGCACA | 3142 |
| 55 | brain-mir-199 | CACUCUGGACUCUGAAUC | 3076 |
| 56 | brain-mir-283 | CGGCGGCGGCGGCGGCGGCGGC | 3005 |
| 57 | brain-mir-219 | UCAAGUGUCAUCUGUCCCUAGG | 2950 |
| 58 | brain-mir-100 | AGUCUUGCUCUGACGCCCAG | 2935 |
| 59 | brain-mir-279 | AUCCCACCGCUGCCACAC | 2835 |
| 60 | brain-mir-162* | UGUUUAGUACUUGGAUGGG | 2742 |
| 61 | brain-mir-115 | AGGCCACAAGCUCUGCACCCA | 2729 |
| 62 | brain-mir-345 | AGGAGUUCUGGGCUGUAGUGCU | 2560 |
| 63 | brain-mir-2 | CCUCUCCUAACCUCGCUCUCG | 2309 |
| 64 | brain-mir-310 | UCUGGGCAACAAAGUUAGA | 2307 |
| 65 | brain-mir-258 | AUCCCACCCCUGCCCCCA | 2265 |
| 66 | brain-mir-240 | UCUGGGCAACAAGGUGAGA | 2250 |
| 67 | brain-mir-271 | UCUGGGCAACCAAGUGAGA | 2248 |
| 68 | brain-mir-18 | UAACUCUUAGAAUCCCCAAAG | 2176 |
| 69 | brain-mir-73 | UCCGGAUGUGCUGACCCCUGCG | 2170 |
| 70 | brain-mir-57 | UCCCUGUCCUCCAGGAGCU | 2159 |
| 71 | brain-mir-25 | ACCCCUUCGGCUGCUGGGCCA | 2147 |
| 72 | brain-mir-161 | CUUCGAAAGCGGCUUCGGCU | 2142 |
| 73 | brain-mir-173 | CCCAGGAGUUCUGGGCUUUAGUG | 2137 |
| 74 | brain-mir-269 | CCCAGGAGUGCUGGGCUGUAGUG | 2131 |
| 75 | brain-mir-399 | CACUGCAACCUCUGCCUCC | 2117 |

TABLE 1-continued

Novel miRNA markers

| SEQ ID NO | miRNA | sequence | readcount |
|---|---|---|---|
| 76 | brain-mir-66 | CCCAGGAGUUUUGGGCUGUAGUG | 2111 |
| 77 | brain-mir-150 | UGAGGUAGUAGGUGGUGUGC | 2086 |
| 78 | brain-mir-133 | UCCCUGUCCUCUAGGAGCU | 2078 |
| 79 | brain-mir-329 | UCGAGGACCCCCCUGCCUGG | 2036 |
| 80 | brain-mir-23 | UUAGUGGCUCCCUCUGCCUGCA | 2029 |
| 81 | brain-mir-29 | CCUGCCCCUCAUCCAGCCCCA | 2017 |
| 82 | brain-mir-104 | UCCGGUAGGGUUCGGGCCUUCC | 1990 |
| 83 | brain-mir-14 | GGGAGAGAACGCGGUCUGAGUGGU | 1942 |
| 84 | brain-mir-145 | AAGCACUGCCUUUGAACCUGA | 1850 |
| 85 | brain-mir-201 | CACCCCACCAGUGCAGGCUG | 1755 |
| 86 | brain-mir-303 | CUCCCACCGCUGCCUCCA | 1749 |
| 87 | brain-mir-331 | CACGCACCUGUAGUCUCAGCU | 1645 |
| 88 | brain-mir-332 | GUCCAUUUUACAGAGCGCUGAU | 1614 |
| 89 | brain-mir-147 | CCCGCACCUGUAGUCUCAGCU | 1497 |
| 90 | brain-mir-187 | AUCCCAGGUCAAGGCUGCAGUGA | 1461 |
| 91 | brain-mir-18* | UUUGGGGAUUCUAAGAGGAAGA | 1385 |
| 92 | brain-mir-339 | GUAGUCGUGGCCGAGUGGUUAAG | 1375 |
| 93 | brain-mir-92 | CCUGGGCAACAGAGCGAGACU | 1348 |
| 94 | brain-mir-229 | AUCCCACCUCUGCUACCA | 1338 |
| 95 | brain-mir-101 | AGACCUACUUAUCUACCAACA | 1335 |
| 96 | brain-mir-55 | UCCCCAACCCCUGCCCGCAGA | 1286 |
| 97 | brain-mir-24 | UAUCCGCUGGCUUACUCUCU | 1254 |
| 98 | brain-mir-346 | CUGCAGACUCGACCUCCCAGGC | 1253 |
| 99 | brain-mir-250* | GUUUGGGCCUGGUUAGUAC | 1251 |
| 100 | brain-mir-184* | GGCUCGUUGGUCUAGGGGUAUGAUUC | 1242 |
| 101 | brain-mir-427 | UCAGAACCGACCGCCUCCCAGC | 1166 |
| 102 | brain-mir-379 | AACCCGGCCCUCCUUGUCCACA | 1150 |
| 103 | brain-mir-41* | CCCCGCGCAGGUUCGAAUCCUG | 1141 |
| 104 | brain-mir-94 | AAGCCUCUGUCCCCACCCCAGG | 1112 |
| 105 | brain-mir-397* | GUCUGGUCUGAUGGUAGU | 1074 |
| 106 | brain-mir-52 | CUGCACUCCAGCCUGGGCGAC | 1015 |
| 107 | brain-mir-112 | AGCUCUGUCUGUGUCUCUAGG | 994 |
| 108 | brain-mir-328 | CCCUGGGGUUCUGAGGACAUGCU | 989 |
| 109 | brain-mir-149 | AAAGUAAUCGCACUUUUUG | 986 |
| 110 | brain-mir-333 | AAAGUAAUCGCAGGUUUUG | 985 |
| 111 | brain-mir-170 | AAAGUAAUGGCAGUUUUUG | 984 |
| 112 | brain-mir-394 | AAAAGUAAUCGUAGUUUUUG | 984 |
| 113 | brain-mir-367 | CCGCCCUCUGUACCUCCCCAGA | 934 |

TABLE 1-continued

Novel miRNA markers

| SEQ ID NO | miRNA | sequence | readcount |
|---|---|---|---|
| 114 | brain-mir-3* | UUUAGUGAGGCCCUCGGAU | 923 |
| 115 | brain-mir-163 | GGCGGCGGCGGCGGCGGC | 919 |
| 116 | brain-mir-136 | CUCCCUCUGAGCCUGCCGCC | 827 |
| 117 | brain-mir-308 | CACUGCACUCCAGCCUGGGUGA | 820 |
| 118 | brain-mir-426 | UUGAGGUCGGACAUGGUGGCU | 809 |
| 119 | brain-mir-396 | CACUGCACUCCAGCCUGGGCAA | 785 |
| 120 | brain-mir-53 | CCCAGGACAGUUUCAGUGAUG | 746 |
| 121 | brain-mir-300 | ACUGCACUCCAGCCUGGGCAA | 741 |
| 122 | brain-mir-378 | CCUCCUCACACCUCUCCUGGCA | 720 |
| 123 | brain-mir-431 | CUCGGCCUUUGCUCGCAGCACU | 716 |
| 124 | brain-mir-27 | ACGCCCCUUCUGAUUCUGCCU | 674 |
| 125 | brain-mir-319 | CUGCACUCCAGCCUGGGCGA | 673 |
| 126 | brain-mir-119 | CACUGCACUCCAGCCUGGGCA | 651 |
| 127 | brain-mir-390 | ACUGCAACCUCCACCUCCUGGGU | 583 |
| 128 | brain-mir-344 | CUCCCUUCCUGCCCCUCAGAGA | 575 |
| 129 | brain-mir-424* | CACUGCACUCCAGCCUGGGUA | 568 |
| 130 | brain-mir-392 | CCCGCCUGUCUCUCUCUUGCA | 557 |
| 131 | brain-mir-188 | CCUGACCCCAUGUCGCCUCUGU | 534 |
| 132 | brain-mir-293 | UUGGUGAGGACCCCAAGCUCGG | 520 |
| 133 | brain-mir-169 | UCCCUGUCACCUCUGGACCUG | 506 |
| 134 | brain-mir-216 | CCCCCCGGAGCGGCCCUGAGA | 500 |
| 135 | brain-mir-199* | AUCUGAGUCACGGCACCA | 492 |
| 136 | brain-mir-262* | UUUAGUGAGGCCCUCUGAU | 484 |
| 137 | brain-mir-380 | AGGCGUUCUGGGCUGUAGUGC | 478 |
| 138 | brain-mir-182 | GAAGCAGCGCCUGUCGCAACUCGCC | 467 |
| 139 | brain-mir-318 | UCUAGAUAGUCAAGUUCUGAUCCAG | 433 |
| 140 | brain-mir-403 | AAAGACUUCCUUCUCUCGCCU | 427 |
| 141 | brain-mir-235 | UCACACCUGUAAUCCCAGCACU | 418 |
| 142 | brain-mir-164 | UCUCACUCUGUUGCCCAGGCUG | 410 |
| 143 | brain-mir-256* | AGCAGGGUGGGGCCUGGUU | 406 |
| 144 | brain-mir-225 | AGUUGCCAGGGCUGCCUUUGGUG | 403 |
| 145 | brain-mir-248 | CUCUCCGCCACCUCCACCGCGG | 399 |
| 146 | brain-mir-170* | GCCGCCAUUACUUUUGCACCAA | 384 |
| 147 | brain-mir-339* | UCUCCCCGCGCAGGUUCGAAU | 371 |
| 148 | brain-mir-79 | CACUGCACUCCAGCCUGGCU | 361 |
| 149 | brain-mir-227 | CUGCACUCCAGCUUGGGCAAC | 356 |
| 150 | brain-mir-299 | CAUGCCACUGCACUCCAGCCU | 353 |

TABLE 1-continued

Novel miRNA markers

| SEQ ID NO | miRNA | sequence | readcount |
|---|---|---|---|
| 151 | brain-mir-412 | UCCCGGACCCAGCCCUCAGGACU | 345 |
| 152 | brain-mir-117 | CAAAACCGCGAUUACUCUUG | 335 |
| 153 | brain-mir-30 | CGGCGGCUCCAGGGACCUGGCG | 334 |
| 154 | brain-mir-294 | UGCACGCGACCAUAGAGCCU | 332 |
| 155 | brain-mir-120 | CACCCAGGCUGGAGUGCAGUG | 326 |
| 156 | brain-mir-263* | ACCUCGGAAGCUAAGCAGGG | 315 |
| 157 | brain-mir-330* | UAACGGACAGAUACGGGGCAGA | 311 |
| 158 | brain-mir-202 | AGCGGAACUUGAGGAGCCGAGA | 301 |
| 159 | brain-mir-188* | GAGAGGAACAUGGGCUCAGGACA | 290 |
| 160 | brain-mir-126 | CUUGAGACUCUGGGUCAGUC | 272 |
| 161 | brain-mir-387 | CAGCGGCUGCGCAUCUCGGG | 270 |
| 162 | brain-mir-287 | AGGCAUUAGAUUCUCAUAAGGA | 268 |
| 163 | brain-mir-398* | UUUCCUUCUCCACUCCCACUGCCUCACU | 264 |
| 164 | brain-mir-323 | CUUAGAGACGGGGUCUUGCU | 263 |
| 165 | brain-mir-224 | UGGUCCAACGACAGGAGUAGG | 259 |
| 166 | brain-mir-187* | CACUGCGCUCCAGCCUGGGCA | 252 |
| 167 | brain-mir-88 | UCUUCACCUGCCUCUGCCUGCA | 249 |
| 168 | brain-mir-96 | AGGCCCUGUCCUCUGCCCCA | 248 |
| 169 | brain-mir-166 | CUGGCUGCUUCCCUUGGUCU | 247 |
| 170 | brain-mir-251 | UGGCCCAAGACCUCAGACC | 233 |
| 171 | brain-mir-380* | GUGCCUGUAGUCCCAGCUACUCAGGAGGCUG | 223 |
| 172 | brain-mir-132 | UGCGCGUCCCGCCCGGUCUGGGA | 212 |
| 173 | brain-mir-99 | UUUAGAGACGGGGACUUGCU | 210 |
| 174 | brain-mir-193 | AUCCCUUUAUCUGUCCUCUAGG | 207 |
| 175 | brain-mir-436 | CACUGCAUUCCAGCCUGGGCGA | 206 |
| 176 | brain-mir-118 | UUCCCUCACUCUUCUCUCAGG | 203 |
| 177 | brain-mir-167 | UCCUCUUAGAAUCCCCAAACC | 202 |
| 178 | brain-mir-161* | CCUCGGCCGCUUUCGAAGCCA | 196 |
| 179 | brain-mir-129 | CAUGGUCCAUUUGCUCUGCU | 194 |
| 180 | brain-mir-381 | UUGCCCAGGCUGGAGUGC | 192 |
| 181 | brain-mir-156 | UCGUAGUCCCUCCGCCGUUUGCA | 190 |
| 182 | brain-mir-311* | ACCCAGGCUGGAGUGCAGUGG | 187 |
| 183 | brain-mir-89 | AAAUACUGAUACAGUGCU | 187 |
| 184 | brain-mir-135 | UCUGACUCUCCGCCUCUCCCCA | 184 |
| 185 | brain-mir-191 | CACCUCCACUGUCCACACUUG | 183 |
| 186 | brain-mir-58 | UCUGCAGGUCUCUGGUGCCU | 178 |
| 187 | brain-mir-179* | CCCCCUUUCCCUGAGCCUGCA | 173 |
| 188 | brain-mir-330 | ACUGCCUUUUGAUGACCGGGAC | 172 |

TABLE 1-continued

Novel miRNA markers

| SEQ ID NO | miRNA | sequence | readcount |
|---|---|---|---|
| 189 | brain-mir-215 | AUUCGCUGGGAAUUCAGCCUCU | 171 |
| 190 | brain-mir-113 | UUCCACUGCCACUACCUAAUU | 168 |
| 191 | brain-mir-245 | UCCUGUGCUGAGCUGCUG | 165 |
| 192 | brain-mir-287* | CCUAUGAGAAUCUAAUGCCUC | 165 |
| 193 | brain-mir-300* | CCCCGGAGGUUGAAGCUACAGUGA | 165 |
| 194 | brain-mir-103 | AAAAACCGUGAUUACUUUUGCA | 159 |
| 195 | brain-mir-35 | UUAUCCUCCAGUAGACUAGGGA | 158 |
| 196 | brain-mir-243 | GAACUCACCCUCUGCUCCCAG | 155 |
| 197 | brain-mir-213 | UGACAGAGCGAGACCUUGUC | 154 |
| 198 | brain-mir-434 | CCUGGCGGCUGUGUCUUCACA | 154 |
| 199 | brain-mir-177 | UGAGCCGGCUGAGCAGGAAGCGG | 152 |
| 200 | brain-mir-322 | UCAGUCCAGUCAUCUCCCUUCA | 149 |
| 201 | brain-mir-33* | CUGGGUGACAGAGCGAGACC | 148 |
| 202 | brain-mir-248* | GGCGGCGGAGGCGGCGGUG | 144 |
| 203 | brain-mir-152 | CUCACACCUGUAAUCCCAGCA | 143 |
| 204 | brain-mir-171 | CCUCUUCCUCCAGCCUCUGAA | 142 |
| 205 | brain-mir-371 | ACUGCAACCUCUGACGCCUGGGU | 140 |
| 206 | brain-mir-162 | CACCCUGAACGCGCCGGC | 136 |
| 207 | brain-mir-207 | UCAGGAGUUUGAGACCAGCCU | 135 |
| 208 | brain-mir-137 | CACCCAGGCUGGAAUGCAGUGG | 134 |
| 209 | brain-mir-123 | CCCCUGGGCUGUUACUGUUCC | 133 |
| 210 | brain-mir-26 | CCAGCUGCCUCUCCUCCAUCG | 133 |
| 211 | brain-mir-343 | AAAAACUGCAAUUUCCUUUGCA | 133 |
| 212 | brain-mir-275 | UAGAACACUCUGGCCCCAUCU | 128 |
| 213 | brain-mir-281 | ACCCUGGCCUCCACUCUGCC | 126 |
| 214 | brain-mir-212 | UCAGGCUUUGCAUCCCGGGACG | 124 |
| 215 | brain-mir-228 | AGGAGGAGGAGGAGGACG | 123 |
| 216 | brain-mir-206 | AAAAGUAAUUGUGGUUUUUG | 119 |
| 217 | brain-mir-318* | UGGAUAUGAUGACUGAUUACCUGAGA | 119 |
| 218 | brain-mir-193* | UUAGAGGCUGGAAUAGAGAUUC | 117 |
| 219 | brain-mir-404 | CCCAUGUCCUGUCUCCUUUUGG | 117 |
| 220 | brain-mir-214 | AGGCUCCAUGACCCCGGCAGG | 116 |
| 221 | brain-mir-334* | AUGUUGACUCUCCUACCUGGGC | 114 |
| 222 | brain-mir-114* | UGAGAGGCAGAGGUUGCAGU | 107 |
| 223 | brain-mir-344* | UUACUGAGGGGAUGAAGGAU | 106 |
| 224 | brain-mir-167* | CUUUGGGGAUUCUAAGAGUUA | 105 |
| 225 | brain-mir-148 | AGACUGACCUUCAACCCCACA | 104 |

TABLE 1-continued

Novel miRNA markers

| SEQ ID NO | miRNA | sequence | readcount |
|---|---|---|---|
| 226 | brain-mir-238 | UUGCAAAGGAAUCCUGGGCC | 98 |
| 227 | brain-mir-278* | UCGACACUUCGAACGCAAU | 96 |
| 228 | brain-mir-130 | CUUCCAUCUCCAUCACCUUGA | 94 |
| 229 | brain-mir-295 | UCUUCAGGAACUCUGGCUAACU | 94 |
| 230 | brain-mir-341 | CACUGCAGACUCCCUGGGCU | 94 |
| 231 | brain-mir-182* | AGAGUUGCUGCCGCUGCUGUC | 92 |
| 232 | brain-mir-118* | UUGAGGGGAGAAUGAGGUGGAG | 90 |
| 233 | brain-mir-305 | ACCUGUGCUUCCUCUUUGA | 90 |
| 234 | brain-mir-183 | AGCGAGGGUUCCGCCGGCCAC | 88 |
| 235 | brain-mir-351 | UGUCUUGCUCUGUUGCCCAGGU | 85 |
| 236 | brain-mir-128 | CUGGCUGUGGGUUCCUUAUCUGU | 84 |
| 237 | brain-mir-350 | AAAAGUAAUUGUGGUUUCUGCC | 84 |
| 238 | brain-mir-407 | UCUGCAGCCCUGGAGCCCCCU | 83 |
| 239 | brain-mir-354 | AAAAGCUGUCCACUGUAGAGU | 80 |
| 240 | brain-mir-356 | GUUCCCUCCACCUCUCAGCA | 76 |
| 241 | brain-mir-349 | UGACUUCUUAUUCUUUCCUGUG | 74 |
| 242 | brain-mir-428 | AUGGCCCUGUGUCUCCUCGGAG | 74 |
| 243 | brain-mir-153 | CCUCUUCUCAGAACACUUCCUGG | 70 |
| 244 | brain-mir-355 | CCCACCUCGGCCUCCCAAAGUGC | 70 |
| 245 | brain-mir-375* | CUGUUCUCUGCUCUCCCCGCA | 70 |
| 246 | brain-mir-65 | ACUGGGGAGGACAGCCAUGACAGGA | 70 |
| 247 | brain-mir-165 | ACUUCACCCUCUGCCUCCCGGGU | 66 |
| 248 | brain-mir-224* | CCCUCCUCUCCUGUGGCC | 66 |
| 249 | brain-mir-352 | UCUGUAUUGUGAAUGGGGAA | 66 |
| 250 | brain-mir-391* | CCCAGGCUGGAGUGCAGUG | 65 |
| 251 | brain-mir-422* | UGUGUCCCCAGUGUCUGUU | 65 |
| 252 | brain-mir-371* | CCCAGGCUGGAGUGCAGU | 61 |
| 253 | brain-mir-384 | UGACCAGCUCUCAUCCCCAGCG | 61 |
| 254 | brain-mir-106 | UCCCAAAGAUUGAUAAGCUGUG | 60 |
| 255 | brain-mir-362 | UUGGGAAGAAUUCUGAUAUUGGU | 60 |
| 256 | brain-mir-72* | GACCACACUCCAUCCUGGGC | 60 |
| 257 | brain-mir-22* | GUGUGUGCACCUGUGUCUGU | 59 |
| 258 | brain-mir-242 | UCCCAAACCUUGUCUGGACAUG | 58 |
| 259 | brain-mir-253* | UGCUGCCGCUGCUGUUGCUC | 58 |
| 260 | brain-mir-382 | CUCAACCUCAAAACGGCCCUCC | 58 |
| 261 | brain-mir-72 | GAGCCCGGGAGGCAGAGGUUG | 58 |
| 262 | brain-mir-415 | UGGGGCCCAGGAAUCUGCAUU | 55 |
| 263 | brain-mir-359 | UCCAAUCACACUUCGUUGCCUGA | 54 |

TABLE 1-continued

Novel miRNA markers

| SEQ ID NO | miRNA | sequence | readcount |
|---|---|---|---|
| 264 | brain-mir-212* | CUCCCGGGAUCCGAAGCUG | 53 |
| 265 | brain-mir-353 | UUCCCUCAGUUAACUUUCCUG | 53 |
| 266 | brain-mir-369* | UGCCCAGGCUGCAGUGCAGUGG | 51 |
| 267 | brain-mir-52* | AACCCAGGACGCCGAGCU | 51 |
| 268 | brain-mir-33 | CAGGUCUCGCUUUGUCACCCAGGC | 49 |
| 269 | brain-mir-104* | GAAGACCCGAGCCUGCCGGGGG | 48 |
| 270 | brain-mir-112* | UUAGGGAGGCGAGAUUGAGC | 48 |
| 271 | brain-mir-155 | UGACUUCUGCCUUCCCAGAGU | 47 |
| 272 | brain-mir-2* | AGAGUCGAGAGUGGGAGAAGAGC | 47 |
| 273 | brain-mir-365 | UGGCUCAGCUCCAAUUCUGCCCACG | 47 |
| 274 | brain-mir-360 | UGCUGAAAGCCGUUUCCCGUGUU | 46 |
| 275 | brain-mir-174 | UCUCAUGGACUCCGCCCACA | 45 |
| 276 | brain-mir-183* | UGGCCGAGCGCGGCUCGUCGCC | 44 |
| 277 | brain-mir-346* | CUGGGAGGUCAAGGCUGCAGUGUC | 44 |
| 278 | brain-mir-116* | CCUGGCGUGGACGACUGGCC | 42 |
| 279 | brain-mir-132* | CCGGCCUCGCGAGCGUCGCGCAGU | 41 |
| 280 | brain-mir-419* | CUCUGCCCUUGGCCUCCCCAG | 41 |
| 281 | brain-mir-131 | CGCCGCUUUCUGGGCUCGCUCA | 40 |
| 282 | brain-mir-363* | UGGCUGUGUGGCUGCUCUGG | 36 |
| 283 | brain-mir-364 | CAGGCUGGAGUGCAGUGG | 36 |
| 284 | brain-mir-65* | CCGCUUCGCUGCCCUUCCCAGA | 36 |
| 285 | brain-mir-105* | UAAUUUCUGAUGCUCUUCCCCU | 35 |
| 286 | brain-mir-230 | UGAGGAGGAUCUGAAGGAUUGG | 35 |
| 287 | brain-mir-237* | UGUCCCUAGCCACCCCAGCA | 35 |
| 288 | brain-mir-274 | UCUGCAGCCUACCUCAUCAGAC | 32 |
| 289 | brain-mir-117* | AAAGUAAUUGUGGUUUUUGCA | 31 |
| 290 | brain-mir-130* | UGAGGUGACCGCAGAUGGGA | 31 |
| 291 | brain-mir-181* | CUCAGUGAUGAAAACUUUGUCCAGU | 31 |
| 292 | brain-mir-319* | AACUCAGGAGGCAGAACUUGCA | 31 |
| 293 | brain-mir-355* | AUUUUUAGUAGAGAUGGGGUUU | 31 |
| 294 | brain-mir-191* | AAGUGUGGGCUCUAGAGUUGG | 30 |
| 295 | brain-mir-243* | AGGGAACAGCUGGGUGAGCU | 30 |
| 296 | brain-mir-26* | AUGGGCAGAAGGGCAGCUGACA | 30 |
| 297 | brain-mir-363 | UGUCAGGGCUGGACACAGCUGCA | 30 |
| 298 | brain-mir-377* | CAUCCAGGGUCCUCACUGCCUGUC | 30 |
| 299 | brain-mir-148* | UUGGGGUUUGGGGUGCAGACA | 29 |
| 300 | brain-mir-352* | UACCCCAUAUACACCUCAGCU | 29 |

TABLE 1-continued

Novel miRNA markers

| SEQ ID NO | miRNA | sequence | readcount |
|---|---|---|---|
| 301 | brain-mir-414 | UCCCUGUCCUUCUCCAGGCU | 29 |
| 302 | brain-mir-113* | AUUAGGUAGUGGCAGUGGAACA | 28 |
| 303 | brain-mir-123* | GACAGUAACAGCCCGGGACAG | 28 |
| 304 | brain-mir-230* | AAACCUCCACUUCCUCCUCA | 27 |
| 305 | brain-mir-30* | CGAGGCCCCAUGGCGCCGCCC | 27 |
| 306 | brain-mir-382* | AGGGCCGGUUCUGAGGUUGAGU | 26 |
| 307 | brain-mir-201* | ACGUGCUGGUCUGUGUGCUGGC | 25 |
| 308 | brain-mir-419 | AGGGCCGAAGGGUGGAAGCU | 25 |
| 309 | brain-mir-194 | CCAAGAGCCUGGAACUGCACC | 24 |
| 310 | brain-mir-34* | GUUGUAGUCCGUGCGAGAAUA | 24 |
| 311 | brain-mir-430 | AUUGCACUCCAGCCUGGG | 24 |
| 312 | brain-mir-66* | CUAUAGUUCCAGCUACUCAGGAGGCU | 24 |
| 313 | brain-mir-324* | UGAUCUCCGCUCACUGCAAGCUCG | 23 |
| 314 | brain-mir-213* | CCAAGUCUUAAUCUGUCAUCC | 22 |
| 315 | brain-mir-360* | AUGCUGGCGCUUUCACACACUC | 22 |
| 316 | brain-mir-411 | CACUGCAGUACUGUGCUGGCA | 22 |
| 317 | brain-mir-206* | AAAAACCACGAUCACUUUUGCA | 21 |
| 318 | brain-mir-328* | UGAUGUCCUCUGUUCCUCAG | 21 |
| 319 | brain-mir-159* | CUGGGGAUGGGAACUGUUGGGA | 20 |
| 320 | brain-mir-219* | UUGGGAUUGACGCCACAUGUCU | 20 |
| 321 | brain-mir-411* | UCCAGACACUGUGGACUGCAGGA | 20 |
| 322 | brain-mir-90 | CCAUGGAUAUCUAGGCUCC | 20 |
| 323 | brain-mir-165* | UCGCCAGGCUGGAGUGUAGUGG | 19 |
| 324 | brain-mir-341* | ACCCAGGUUGGAGUGCAGU | 19 |
| 325 | brain-mir-399* | AGGCUGGAGUGCAGUGGUGC | 19 |
| 326 | brain-mir-421 | CGCUGACCCGCCUUCUCCGCA | 19 |
| 327 | brain-mir-425 | CCUGGCAAUACACAUCUACUG | 19 |
| 328 | brain-mir-172 | CUUGUUGAUGUGCUGCGCCU | 18 |
| 329 | brain-mir-298* | CCCGGGUUCAAGUGAUUCU | 18 |
| 330 | brain-mir-73* | UCAGGGCGAAGCUUAUCCAUUGC | 18 |
| 331 | brain-mir-207* | AAGGCUCAAACUCCUGAACUCA | 17 |
| 332 | brain-mir-239* | UCCCAGGUUCAAGCAAUUCUCC | 17 |
| 333 | brain-mir-369 | UCCCUGCAACCUAGAGCUC | 17 |
| 334 | brain-mir-390* | CCCAGGCUGGAAUGCAAUGGC | 17 |
| 335 | brain-mir-395* | GCCCCAGAGCCGGAGGCUGCAGUG | 17 |
| 336 | brain-mir-125 | CUGGAGAGAAAGGCAGUCAGAGG | 16 |
| 337 | brain-mir-131* | UGCGGGCCCUGGGAGUGGAGAC | 16 |
| 338 | brain-mir-14* | CAUUGAUGAUCGUUCUUCUCUCCGUA | 16 |

TABLE 1-continued

Novel miRNA markers

| SEQ ID NO | miRNA | sequence | readcount |
|---|---|---|---|
| 339 | brain-mir-374 | UUUCACUGAUGUGCUCCACU | 16 |
| 340 | brain-mir-99* | CAAUCCUCCCACCUCGGCC | 16 |
| 341 | brain-mir-242* | UGUCUAGACAAGGCUGGGGAAAU | 15 |
| 342 | brain-mir-254* | ACGGCGUGACACAUCUUCUGU | 15 |
| 343 | brain-mir-280* | UGCCCGUGAGCUCCACCUGCCUGC | 15 |
| 344 | brain-mir-320* | UGGGUGACAGAGUGAGACCCC | 15 |
| 345 | brain-mir-416 | AUUGGCACUGCACAUGAUUG | 15 |
| 346 | brain-mir-63* | CACUGCACUCCAGCUUGGAUG | 15 |
| 347 | brain-mir-109 | GCUCCACUUUCAGUUCUCUUG | 14 |
| 348 | brain-mir-227* | AGCCCAGGAGGUCGGGACUGCA | 14 |
| 349 | brain-mir-108* | AGGAGUGGGGGUGGGACGUAAG | 13 |
| 350 | brain-mir-109* | AGAGAACUAAAACUGGAGUCU | 13 |
| 351 | brain-mir-225* | CCAGAGCAGCCUGCGGUAACAGU | 13 |
| 352 | brain-mir-255* | UCCCAGGUUCAAGCAAUUCUUC | 13 |
| 353 | brain-mir-46* | GCUUACGCCUGUAAUCCC | 13 |
| 354 | brain-mir-214* | GCUGCGUUUCAUGGAGCCCCU | 12 |
| 355 | brain-mir-279* | GUGGUCUAAGGCGCUGGAUUU | 12 |
| 356 | brain-mir-381* | ACCUUCAACCUCCCGGGCUC | 12 |
| 357 | brain-mir-418* | AGGCCAUUCCCCAUCAGAUGA | 12 |
| 358 | brain-mir-53* | UCAGCUGAAACAGUCCUGGAC | 12 |
| 359 | brain-mir-107 | UUCCCCGCUUCCCCCCUAGGG | 11 |
| 360 | brain-mir-111* | UCACUAAAGUUGGUAUACA | 11 |
| 361 | brain-mir-147* | UGGAGGUUGCAGUGAGCUGAGA | 11 |
| 362 | brain-mir-275* | GAUGGGAUCGGAGCUCUAGAGU | 11 |
| 363 | brain-mir-119* | CCCGGGGUCGAGACUGCAGUGAG | 10 |
| 364 | brain-mir-211* | CACCUGGGUUGUCCCCUCUAG | 10 |
| 365 | brain-mir-310* | CUGCAGUGAGCUGAGAUUGUG | 10 |

These 365 miRNA markers have the corresponding sequences SEQ ID NO 1 to SEQ ID NO 365 in the attached sequence protocol. These novel miRNA markers were compared in subjects with Alzheimer's Disease (AD) and healthy controls.

To detect potential biomarker candidates, for example expression levels in Alzheimer Disease patients and controls were compared and two-tailed t-tests and adjusted the significance values for multiple testing using Benjamini Hochberg adjustment were computed. All markers with adjusted significance values below 0.05 were considered statistically significant. Additionally, the area under the receiver operator characteristics curve (AUC) was computed to understand the specificity and sensitivity of miRNAs for Alzheimer diagnosis. Altogether, 58 significantly dys-regulated miRNAs were detected, 48 markers were significantly up-regulated in Alzheimer, while 10 were significantly down-regulated. A list of the respective markers is presented in Table 2 and 3.

TABLE 2

Upregulated Markers

| Marker | median AD | median Control | t-test p-value single | t-test p-value adjusted | AUC |
|---|---|---|---|---|---|
| brain-mir-102 | 34.05263158 | 22.92293233 | 0.001143055 | 0.009324728 | 0.757102273 |
| brain-mir-111 | 986.4774436 | 590.4022556 | 0.000471376 | 0.004863495 | 0.750473485 |
| brain-mir-112 | 10.2424812 | 3.268796992 | 2.77E-08 | 1.05E-05 | 0.873579545 |
| brain-mir-114 | 1009.646617 | 543.5526316 | 5.76E-05 | 0.001147203 | 0.685606061 |
| brain-mir-12 | 2433.041353 | 1370.533835 | 9.13E-05 | 0.001569161 | 0.722064394 |
| brain-mir-129 | 1.231203008 | 0.813909774 | 0.005286528 | 0.030228152 | 0.655776515 |
| brain-mir-153 | 0.57518797 | 0.142857143 | 0.000847895 | 0.007436035 | 0.686079545 |
| brain-mir-160 | 13.16353383 | 9.364661654 | 0.004731412 | 0.028227537 | 0.649621212 |
| brain-mir-161 | 17.4887218 | 10.5 | 0.002418537 | 0.016536723 | 0.742424242 |
| brain-mir-166 | 2.421052632 | 1.092105263 | 0.000624293 | 0.005914566 | 0.714962121 |
| brain-mir-188 | 4.323308271 | 2.359022556 | 0.002061148 | 0.014577638 | 0.690340909 |
| brain-mir-189 | 4.323308271 | 2.359022556 | 0.002061148 | 0.014577638 | 0.690340909 |
| brain-mir-190 | 4.323308271 | 2.359022556 | 0.002061148 | 0.014577638 | 0.690340909 |
| brain-mir-192 | 4.323308271 | 2.359022556 | 0.002061148 | 0.014577638 | 0.690340909 |
| brain-mir-193 | 1.612781955 | 0.840225564 | 0.000633944 | 0.005914566 | 0.700284091 |
| brain-mir-200 | 30.37406015 | 15.82330827 | 5.41E-05 | 0.001147203 | 0.76657197 |
| brain-mir-201 | 15.42481203 | 9.546992481 | 0.000293033 | 0.003671284 | 0.729166667 |
| brain-mir-219 | 28.57518797 | 15.78195489 | 0.000144143 | 0.00223636 | 0.773674242 |
| brain-mir-220 | 36.45300752 | 24.45112782 | 0.001008503 | 0.008423399 | 0.718276515 |
| brain-mir-23 | 16.22180451 | 11.36654135 | 0.002471274 | 0.016671592 | 0.71875 |
| brain-mir-232 | 75.07330827 | 39.92857143 | 9.70E-05 | 0.001635526 | 0.679924242 |
| brain-mir-247 | 2997.969925 | 1634.68797 | 7.23E-05 | 0.001320329 | 0.731534091 |
| brain-mir-251 | 1.890977444 | 0.845864662 | 0.000568855 | 0.005598206 | 0.729640152 |
| brain-mir-258 | 5.697368421 | 0.823308271 | 0.007901589 | 0.042254229 | 0.720170455 |
| brain-mir-279 | 10.13345865 | 5.154135338 | 0.000437069 | 0.004618187 | 0.695549242 |
| brain-mir-293 | 3.402255639 | 2.005639098 | 0.004353366 | 0.026513209 | 0.687973485 |
| brain-mir-299 | 3.958646617 | 1.785714286 | 0.000839426 | 0.007436035 | 0.706912879 |
| brain-mir-308 | 7.87593985 | 4.323308271 | 8.18E-06 | 0.000174073 | 0.793560606 |
| brain-mir-311 | 382.2819549 | 266.924812 | 0.00228615 | 0.016039629 | 0.637310606 |
| brain-mir-314 | 3614.804511 | 2124.575188 | 8.13E-05 | 0.001425929 | 0.732481061 |
| brain-mir-319 | 4.954887218 | 3.686090226 | 0.003165849 | 0.020566296 | 0.691287879 |
| brain-mir-351 | 0.272556391 | 0.127819549 | 0.002677002 | 0.017785842 | 0.643939394 |
| brain-mir-390 | 5.419172932 | 3.142857143 | 8.85E-05 | 0.000935541 | 0.761837121 |
| brain-mir-392 | 5.569548872 | 3.144736842 | 0.001117105 | 0.009242463 | 0.658617424 |
| brain-mir-395 | 7.87593985 | 4.323308271 | 8.18E-06 | 0.000174073 | 0.793560606 |
| brain-mir-399 | 19.16165414 | 12.77067669 | 0.001584551 | 0.012039621 | 0.661931818 |
| brain-mir-403 | 4.184210526 | 2.836466165 | 0.001640863 | 0.012299462 | 0.669507576 |
| brain-mir-41S | 10.57330827 | 5.919172932 | 0.000257097 | 0.00331579 | 0.78030303 |
| brain-mir-424S | 4.857142857 | 2.150375940 | 0.000113425 | 0.001856876 | 0.760890152 |
| brain-mir-431 | 6.246240602 | 2.943609023 | 8.30E-06 | 0.000324387 | 0.786931818 |
| brain-mir-52 | 9.240601504 | 4.650375940 | 0.00020654 | 0.002825926 | 0.781723485 |
| brain-mir-53 | 6.746240602 | 3.890977444 | 0.000209767 | 0.002825926 | 0.760416667 |
| brain-mir-72S | 0.443609023 | 0.124060150 | 0.001422557 | 0.011139131 | 0.734848485 |
| brain-mir-73 | 21.17669173 | 12.9924812 | 0.001695821 | 0.012497773 | 0.692234848 |
| brain-mir-79 | 3.520676692 | 1.302631572 | 9.85E-05 | 0.000781186 | 0.755208333 |
| brain-mir-80 | 3.520676692 | 1.302631572 | 9.85E-05 | 0.000781186 | 0.755208333 |
| brain-mir-83 | 160.5808271 | 95.38721805 | 1.37E-05 | 0.000481771 | 0.736742424 |
| brain-mir-88 | 2.364661654 | 1.377819549 | 0.000568108 | 0.005598206 | 0.691287879 |

TABLE 3

Downregulated Markers

| Marker | median AD | median Control | t-test p-value single | t-test p-value adjusted | AUC |
|---|---|---|---|---|---|
| brain-mir-145 | 13.95112782 | 17.7556391 | 0.008979579 | 0.04687554 | 0.314394 |
| brain-mir-149 | 2.815789474 | 7.836466165 | 0.000344696 | 0.003925953 | 0.209754 |
| brain-mir-150 | 6.426691729 | 19.48120301 | 0.003450184 | 0.021867415 | 0.22017 |
| brain-mir-151 | 2.815789474 | 7.836466165 | 0.000344696 | 0.003925953 | 0.209754 |
| brain-mir-170 | 2.802631579 | 7.836466165 | 0.000324105 | 0.003841085 | 0.206913 |
| brain-mir-248S | 0.244360902 | 0.928571429 | 0.006543868 | 0.036322611 | 0.254735 |
| brain-mir-333 | 2.802631579 | 7.836466165 | 0.00041227 | 0.004463708 | 0.206913 |
| brain-mir-370 | 178.4586466 | 778.2894737 | 0.000362522 | 0.004024449 | 0.155303 |
| brain-mir-394 | 2.802631579 | 7.836466165 | 0.000316457 | 0.003841085 | 0.205966 |
| brain-mir-398 | 10.03383459 | 29.55263158 | 0.00168198 | 0.012497773 | 0.196496 |

Besides single markers, combinations of multiple markers have demonstrated a potential to improve the diagnostic accuracy.

Validation of signature by q-RT-PCR

In order to transfer the signature to clinical routine settings it is essential that the proposed in-vitro diagnostic test can be applied in molecular diagnostic labs in reasonable time using standard equipment. To this end, qRT-PCR represents a suitable solution to replicate and validate markers using this approach. In addition to measure just controls, AD and MCI patients, a wide range of other neurological disorders were also included.

First, the fold quotients of the initial screening cohort were compared and analyzed by next-generation sequencing and this was compared to the performance of the same miRNAs by qRT-PCR. As for the next generation sequencing screening approach AUC values were calculated for the validation qRT-PCR cohort. The best single miRNA was brain-mir 112 with an AUC of 87.5%.

While averaged values of 0.087 and standard deviation of 0.72 for the controls and average values of 0.22 and standard deviation of 0.74 were reached for the MCI patients, AD patients reached a much higher score of 0.63 at a standard deviation of 0.64.

Scores of Other Neurological Disorders

Figure 2:
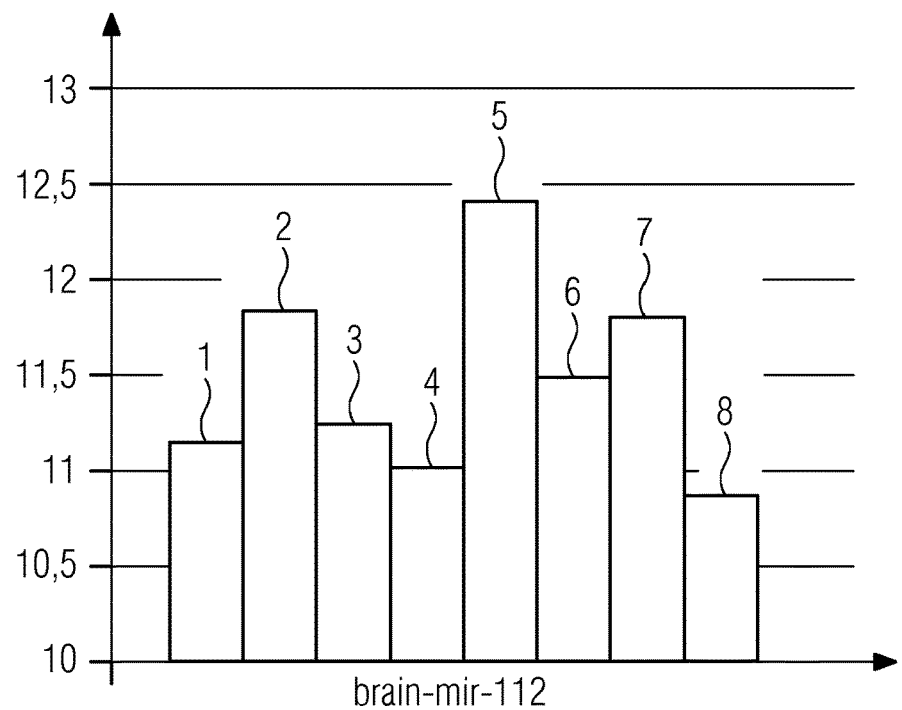
FIG. 2 shows delta CT values (y-axis) of a first exemplary novel nucleic acid molecule miRNA marker of the invention in different samples (1-8) of patients having different neuronal disorders and controls.
Figure 3:
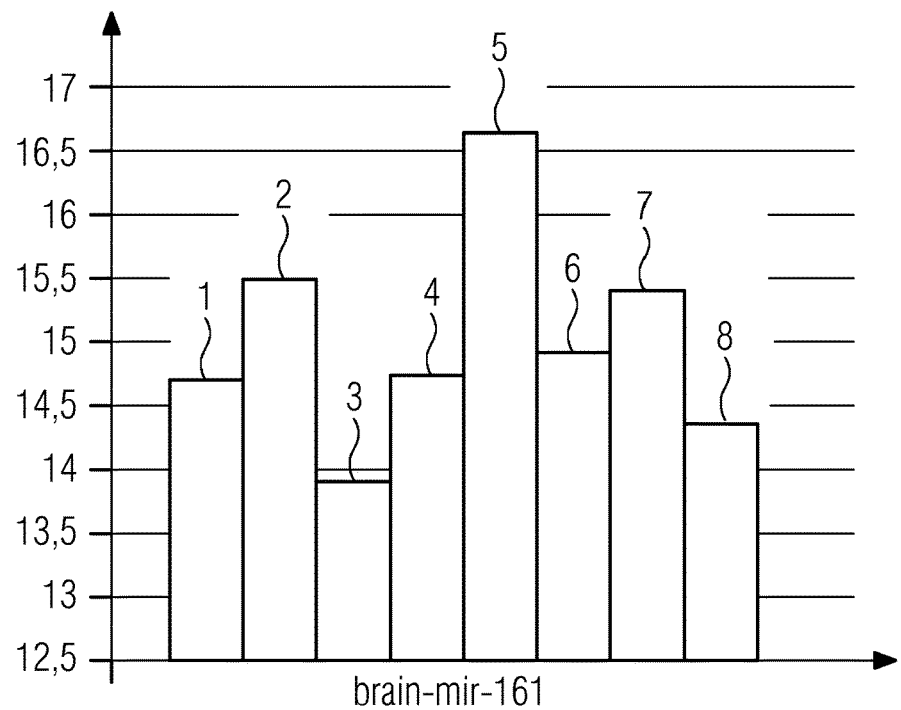
FIG. 3 shows delta CT values (y-axis) of a further exemplary novel nucleic acid molecule miRNA marker of the invention in different samples (1-8) of patients having different neuronal disorders and controls.

For 2 different miRNAs (brain-mir-161 and brain-mir-112, it was demonstrated that these miRNAs have significant information content to distinguish between Alzheimer and Controls (p<0.05) and also between most other neurological disorders, providing evidence for them as general disease markers (FIG. 2 and FIG. 3).

Thus it is shown that the nucleic acid molecules of the invention are useful for evaluating a physiological and/or pathological condition of a subject.

Further, the nucleic acid molecules of the invention can be used for the manufacture of a pharmaceutical composition.

Such a composition can be used for diagnostic and/or therapeutic applications, e.g. to diagnose or monitor disease, or to modulate gene expression.

Further, the nucleic acid molecules of the invention can be used in kit comprising means for determining the presence and/or amount of an expression level of at least one nucleic acid molecule of the invention. Such a kit can comprise a probe or a set of probes for detecting and/or quantifying at least one nucleic acid molecules of the invention, e.g. as part of a set of primers/probes for PCR detection, as probe for an array based detection or for hybridization based detection.

What is claimed is:

1. A pharmaceutical composition containing an isolated nucleic acid molecule consisting of SEQ ID NO:270, wherein at least one nucleotide of the isolated nucleic acid molecule is a modified nucleotide or nucleotide analog.

\* \* \* \* \*

SEQUENCE LISTING

```
<160> NUMBER OF SEQ ID NOS: 365

<210> SEQ ID NO 1
<211> LENGTH: 24
<212> TYPE: RNA
<213> ORGANISM: Homo sapiens

<400> SEQUENCE: 1
acucccacug cuucacuuga uuag                                              24

<210> SEQ ID NO 2
<211> LENGTH: 24
<212> TYPE: RNA
<213> ORGANISM: Homo sapiens

<400> SEQUENCE: 2
acgcccacug cuucacuuga cuag                                              24

<210> SEQ ID NO 3
<211> LENGTH: 24
<212> TYPE: RNA
<213> ORGANISM: Homo sapiens

<400> SEQUENCE: 3
acucccacug cuugacuuga cuag                                              24

<210> SEQ ID NO 4
<211> LENGTH: 23
<212> TYPE: RNA
<213> ORGANISM: Homo sapiens

<400> SEQUENCE: 4
ggaauaccgg gugcuguagg cuu                                               23

<210> SEQ ID NO 5
<211> LENGTH: 19
<212> TYPE: RNA
<213> ORGANISM: Homo sapiens
```

```
<400> SEQUENCE: 5
ugccugucug agcgucgcu                                              19

<210> SEQ ID NO 6
<211> LENGTH: 21
<212> TYPE: RNA
<213> ORGANISM: Homo sapiens

<400> SEQUENCE: 6
ucgaucccca uccucgucgc u                                           21

<210> SEQ ID NO 7
<211> LENGTH: 22
<212> TYPE: RNA
<213> ORGANISM: Homo sapiens

<400> SEQUENCE: 7
cacugcuaaa uuuggcuggc uu                                          22

<210> SEQ ID NO 8
<211> LENGTH: 20
<212> TYPE: RNA
<213> ORGANISM: Homo sapiens

<400> SEQUENCE: 8
auaacgggug cguaggcuu                                              20

<210> SEQ ID NO 9
<211> LENGTH: 22
<212> TYPE: RNA
<213> ORGANISM: Homo sapiens

<400> SEQUENCE: 9
cacugcaacc ucugccuccg gu                                          22

<210> SEQ ID NO 10
<211> LENGTH: 24
<212> TYPE: RNA
<213> ORGANISM: Homo sapiens

<400> SEQUENCE: 10
ggcuggucug augguagugg guua                                        24

<210> SEQ ID NO 11
<211> LENGTH: 21
<212> TYPE: RNA
<213> ORGANISM: Homo sapiens

<400> SEQUENCE: 11
acugcuaaau uugacuagcu a                                           21

<210> SEQ ID NO 12
<211> LENGTH: 22
<212> TYPE: RNA
<213> ORGANISM: Homo sapiens

<400> SEQUENCE: 12
uuucgauggu agucgccgug cc                                          22

<210> SEQ ID NO 13
<211> LENGTH: 22
<212> TYPE: RNA
<213> ORGANISM: Homo sapiens
```

```
<400> SEQUENCE: 13
cacugcaacc ucugccuccc ga                                          22

<210> SEQ ID NO 14
<211> LENGTH: 23
<212> TYPE: RNA
<213> ORGANISM: Homo sapiens

<400> SEQUENCE: 14
ccucaccauc ccuucugccu gca                                         23

<210> SEQ ID NO 15
<211> LENGTH: 22
<212> TYPE: RNA
<213> ORGANISM: Homo sapiens

<400> SEQUENCE: 15
uuuccucugc ucucauacca ca                                          22

<210> SEQ ID NO 16
<211> LENGTH: 23
<212> TYPE: RNA
<213> ORGANISM: Homo sapiens

<400> SEQUENCE: 16
ccucaccacc ccuucugccu gca                                         23

<210> SEQ ID NO 17
<211> LENGTH: 21
<212> TYPE: RNA
<213> ORGANISM: Homo sapiens

<400> SEQUENCE: 17
ucaccacccc uucugccugc a                                           21

<210> SEQ ID NO 18
<211> LENGTH: 21
<212> TYPE: RNA
<213> ORGANISM: Homo sapiens

<400> SEQUENCE: 18
cacugcaacc ucugccuccu g                                           21

<210> SEQ ID NO 19
<211> LENGTH: 20
<212> TYPE: RNA
<213> ORGANISM: Homo sapiens

<400> SEQUENCE: 19
cagggucucg uucuguugcc                                             20

<210> SEQ ID NO 20
<211> LENGTH: 21
<212> TYPE: RNA
<213> ORGANISM: Homo sapiens

<400> SEQUENCE: 20
cacugcuacc ucugccuccg g                                           21

<210> SEQ ID NO 21
<211> LENGTH: 21
<212> TYPE: RNA
```

<213> ORGANISM: Homo sapiens

<400> SEQUENCE: 21
ucugggcauc aaagugagac c                                              21

<210> SEQ ID NO 22
<211> LENGTH: 21
<212> TYPE: RNA
<213> ORGANISM: Homo sapiens

<400> SEQUENCE: 22
ucugggcaac agagugagac c                                              21

<210> SEQ ID NO 23
<211> LENGTH: 21
<212> TYPE: RNA
<213> ORGANISM: Homo sapiens

<400> SEQUENCE: 23
ucugggcaac aaagugauac c                                              21

<210> SEQ ID NO 24
<211> LENGTH: 21
<212> TYPE: RNA
<213> ORGANISM: Homo sapiens

<400> SEQUENCE: 24
ucugggcaac aaggugagac c                                              21

<210> SEQ ID NO 25
<211> LENGTH: 24
<212> TYPE: RNA
<213> ORGANISM: Homo sapiens

<400> SEQUENCE: 25
cugagaagac agucgaacuu gacu                                           24

<210> SEQ ID NO 26
<211> LENGTH: 19
<212> TYPE: RNA
<213> ORGANISM: Homo sapiens

<400> SEQUENCE: 26
gucuacgacc auaccaccc                                                 19

<210> SEQ ID NO 27
<211> LENGTH: 19
<212> TYPE: RNA
<213> ORGANISM: Homo sapiens

<400> SEQUENCE: 27
ucaaaucccg gacgagccc                                                 19

<210> SEQ ID NO 28
<211> LENGTH: 21
<212> TYPE: RNA
<213> ORGANISM: Homo sapiens

<400> SEQUENCE: 28
agucuugcuc ugucgcccag g                                              21

<210> SEQ ID NO 29
<211> LENGTH: 25

```
<212> TYPE: RNA
<213> ORGANISM: Homo sapiens

<400> SEQUENCE: 29
gcggcggcgg cggcggcggc ggcgg                                          25

<210> SEQ ID NO 30
<211> LENGTH: 20
<212> TYPE: RNA
<213> ORGANISM: Homo sapiens

<400> SEQUENCE: 30
aagguagaua gaacaggucu                                                20

<210> SEQ ID NO 31
<211> LENGTH: 22
<212> TYPE: RNA
<213> ORGANISM: Homo sapiens

<400> SEQUENCE: 31
cuuccccacc cucuccugca gc                                             22

<210> SEQ ID NO 32
<211> LENGTH: 20
<212> TYPE: RNA
<213> ORGANISM: Homo sapiens

<400> SEQUENCE: 32
ucaggcuccg uccccucccu                                                20

<210> SEQ ID NO 33
<211> LENGTH: 18
<212> TYPE: RNA
<213> ORGANISM: Homo sapiens

<400> SEQUENCE: 33
ccacccugaa cgcgcccg                                                  18

<210> SEQ ID NO 34
<211> LENGTH: 25
<212> TYPE: RNA
<213> ORGANISM: Homo sapiens

<400> SEQUENCE: 34
cggcggcggc ggcggcggcg gcggc                                          25

<210> SEQ ID NO 35
<211> LENGTH: 22
<212> TYPE: RNA
<213> ORGANISM: Homo sapiens

<400> SEQUENCE: 35
uugcucugcu cucccuugua cu                                             22

<210> SEQ ID NO 36
<211> LENGTH: 20
<212> TYPE: RNA
<213> ORGANISM: Homo sapiens

<400> SEQUENCE: 36
cugguuagua cuuggauggg                                                20

<210> SEQ ID NO 37
```

```
<211> LENGTH: 19
<212> TYPE: RNA
<213> ORGANISM: Homo sapiens

<400> SEQUENCE: 37
gguuaguacu uggauggga                                              19

<210> SEQ ID NO 38
<211> LENGTH: 21
<212> TYPE: RNA
<213> ORGANISM: Homo sapiens

<400> SEQUENCE: 38
uccggauccg gcuccgcgcc u                                           21

<210> SEQ ID NO 39
<211> LENGTH: 25
<212> TYPE: RNA
<213> ORGANISM: Homo sapiens

<400> SEQUENCE: 39
gcggcggcgg cggcggcggc ggagg                                       25

<210> SEQ ID NO 40
<211> LENGTH: 21
<212> TYPE: RNA
<213> ORGANISM: Homo sapiens

<400> SEQUENCE: 40
agucuugcuc ugucgccccg g                                           21

<210> SEQ ID NO 41
<211> LENGTH: 19
<212> TYPE: RNA
<213> ORGANISM: Homo sapiens

<400> SEQUENCE: 41
ucgacuccug gcuggcucg                                              19

<210> SEQ ID NO 42
<211> LENGTH: 22
<212> TYPE: RNA
<213> ORGANISM: Homo sapiens

<400> SEQUENCE: 42
gcggcggcgg cggcggcggc gg                                          22

<210> SEQ ID NO 43
<211> LENGTH: 22
<212> TYPE: RNA
<213> ORGANISM: Homo sapiens

<400> SEQUENCE: 43
uaugucccac ccccacuccu gu                                          22

<210> SEQ ID NO 44
<211> LENGTH: 23
<212> TYPE: RNA
<213> ORGANISM: Homo sapiens

<400> SEQUENCE: 44
ucugaucguu ccccuccgua cag                                         23
```

<210> SEQ ID NO 45
<211> LENGTH: 21
<212> TYPE: RNA
<213> ORGANISM: Homo sapiens

<400> SEQUENCE: 45
agucuugcuc uguugcccag g                                              21

<210> SEQ ID NO 46
<211> LENGTH: 21
<212> TYPE: RNA
<213> ORGANISM: Homo sapiens

<400> SEQUENCE: 46
uauggagguc ucugucuggc u                                              21

<210> SEQ ID NO 47
<211> LENGTH: 21
<212> TYPE: RNA
<213> ORGANISM: Homo sapiens

<400> SEQUENCE: 47
agucuugcuc ugucgcccgg g                                              21

<210> SEQ ID NO 48
<211> LENGTH: 20
<212> TYPE: RNA
<213> ORGANISM: Homo sapiens

<400> SEQUENCE: 48
ucaggcucag uccccuccau                                                20

<210> SEQ ID NO 49
<211> LENGTH: 21
<212> TYPE: RNA
<213> ORGANISM: Homo sapiens

<400> SEQUENCE: 49
agucuugcuc ugucacccag g                                              21

<210> SEQ ID NO 50
<211> LENGTH: 21
<212> TYPE: RNA
<213> ORGANISM: Homo sapiens

<400> SEQUENCE: 50
agucuugcug ugucgcccag g                                              21

<210> SEQ ID NO 51
<211> LENGTH: 23
<212> TYPE: RNA
<213> ORGANISM: Homo sapiens

<400> SEQUENCE: 51
agcccgucgg accuccgcca ugc                                            23

<210> SEQ ID NO 52
<211> LENGTH: 25
<212> TYPE: RNA
<213> ORGANISM: Homo sapiens

<400> SEQUENCE: 52
gcggcggcgg cggcggcggc gcggg                                          25

```
<210> SEQ ID NO 53
<211> LENGTH: 24
<212> TYPE: RNA
<213> ORGANISM: Homo sapiens

<400> SEQUENCE: 53
ggcugguccg agugcagugg uguu                                            24

<210> SEQ ID NO 54
<211> LENGTH: 21
<212> TYPE: RNA
<213> ORGANISM: Homo sapiens

<400> SEQUENCE: 54
uuccuggcuc ucuguugcac a                                               21

<210> SEQ ID NO 55
<211> LENGTH: 18
<212> TYPE: RNA
<213> ORGANISM: Homo sapiens

<400> SEQUENCE: 55
cacucuggac ucugaauc                                                   18

<210> SEQ ID NO 56
<211> LENGTH: 22
<212> TYPE: RNA
<213> ORGANISM: Homo sapiens

<400> SEQUENCE: 56
cggcggcggc ggcggcggcg gc                                              22

<210> SEQ ID NO 57
<211> LENGTH: 22
<212> TYPE: RNA
<213> ORGANISM: Homo sapiens

<400> SEQUENCE: 57
ucaaguguca ucuguccua gg                                               22

<210> SEQ ID NO 58
<211> LENGTH: 20
<212> TYPE: RNA
<213> ORGANISM: Homo sapiens

<400> SEQUENCE: 58
agucuugcuc ugacgcccag                                                 20

<210> SEQ ID NO 59
<211> LENGTH: 18
<212> TYPE: RNA
<213> ORGANISM: Homo sapiens

<400> SEQUENCE: 59
aucccaccgc ugccacac                                                   18

<210> SEQ ID NO 60
<211> LENGTH: 19
<212> TYPE: RNA
<213> ORGANISM: Homo sapiens

<400> SEQUENCE: 60
uguuuaguac uuggaugggg                                                 19
```

<210> SEQ ID NO 61
<211> LENGTH: 21
<212> TYPE: RNA
<213> ORGANISM: Homo sapiens

<400> SEQUENCE: 61
aggccacaag cucugcaccc a         21

<210> SEQ ID NO 62
<211> LENGTH: 22
<212> TYPE: RNA
<213> ORGANISM: Homo sapiens

<400> SEQUENCE: 62
aggaguucug ggcuguagug cu        22

<210> SEQ ID NO 63
<211> LENGTH: 21
<212> TYPE: RNA
<213> ORGANISM: Homo sapiens

<400> SEQUENCE: 63
ccucuccuaa ccucgcucuc g         21

<210> SEQ ID NO 64
<211> LENGTH: 19
<212> TYPE: RNA
<213> ORGANISM: Homo sapiens

<400> SEQUENCE: 64
ucugggcaac aaaguuaga            19

<210> SEQ ID NO 65
<211> LENGTH: 18
<212> TYPE: RNA
<213> ORGANISM: Homo sapiens

<400> SEQUENCE: 65
aucccacccc ugccccca             18

<210> SEQ ID NO 66
<211> LENGTH: 19
<212> TYPE: RNA
<213> ORGANISM: Homo sapiens

<400> SEQUENCE: 66
ucugggcaac aaggugaga            19

<210> SEQ ID NO 67
<211> LENGTH: 19
<212> TYPE: RNA
<213> ORGANISM: Homo sapiens

<400> SEQUENCE: 67
ucugggcaac caagugaga            19

<210> SEQ ID NO 68
<211> LENGTH: 21
<212> TYPE: RNA
<213> ORGANISM: Homo sapiens

<400> SEQUENCE: 68
uaacucuuag aauccccaaa g                                    21

<210> SEQ ID NO 69
<211> LENGTH: 22
<212> TYPE: RNA
<213> ORGANISM: Homo sapiens

<400> SEQUENCE: 69
uccggaugug cugaccccug cg                                   22

<210> SEQ ID NO 70
<211> LENGTH: 19
<212> TYPE: RNA
<213> ORGANISM: Homo sapiens

<400> SEQUENCE: 70
ucccuguccu ccaggagcu                                       19

<210> SEQ ID NO 71
<211> LENGTH: 21
<212> TYPE: RNA
<213> ORGANISM: Homo sapiens

<400> SEQUENCE: 71
accccuucgg cugcugggcc a                                    21

<210> SEQ ID NO 72
<211> LENGTH: 20
<212> TYPE: RNA
<213> ORGANISM: Homo sapiens

<400> SEQUENCE: 72
cuucgaaagc ggcuucggcu                                      20

<210> SEQ ID NO 73
<211> LENGTH: 23
<212> TYPE: RNA
<213> ORGANISM: Homo sapiens

<400> SEQUENCE: 73
cccaggaguu cugggcuuua gug                                  23

<210> SEQ ID NO 74
<211> LENGTH: 23
<212> TYPE: RNA
<213> ORGANISM: Homo sapiens

<400> SEQUENCE: 74
cccaggagug cugggcugua gug                                  23

<210> SEQ ID NO 75
<211> LENGTH: 19
<212> TYPE: RNA
<213> ORGANISM: Homo sapiens

<400> SEQUENCE: 75
cacugcaacc ucugccucc                                       19

<210> SEQ ID NO 76
<211> LENGTH: 23
<212> TYPE: RNA
<213> ORGANISM: Homo sapiens

<400> SEQUENCE: 76
cccaggaguu uugggcugua gug 23

<210> SEQ ID NO 77
<211> LENGTH: 20
<212> TYPE: RNA
<213> ORGANISM: Homo sapiens

<400> SEQUENCE: 77
ugagguagua gguggugugc 20

<210> SEQ ID NO 78
<211> LENGTH: 19
<212> TYPE: RNA
<213> ORGANISM: Homo sapiens

<400> SEQUENCE: 78
ucccuguccu cuaggagcu 19

<210> SEQ ID NO 79
<211> LENGTH: 21
<212> TYPE: RNA
<213> ORGANISM: Homo sapiens

<400> SEQUENCE: 79
ucgaggaccc ccccugccug g 21

<210> SEQ ID NO 80
<211> LENGTH: 22
<212> TYPE: RNA
<213> ORGANISM: Homo sapiens

<400> SEQUENCE: 80
uuaguggcuc ccucugccug ca 22

<210> SEQ ID NO 81
<211> LENGTH: 21
<212> TYPE: RNA
<213> ORGANISM: Homo sapiens

<400> SEQUENCE: 81
ccugccccuc auccagcccc a 21

<210> SEQ ID NO 82
<211> LENGTH: 22
<212> TYPE: RNA
<213> ORGANISM: Homo sapiens

<400> SEQUENCE: 82
uccgguaggg uucgggccuu cc 22

<210> SEQ ID NO 83
<211> LENGTH: 24
<212> TYPE: RNA
<213> ORGANISM: Homo sapiens

<400> SEQUENCE: 83
gggagagaac gcggucugag uggu 24

<210> SEQ ID NO 84
<211> LENGTH: 21
<212> TYPE: RNA
<213> ORGANISM: Homo sapiens

<400> SEQUENCE: 84
aagcacugcc uuugaaccug a                                              21

<210> SEQ ID NO 85
<211> LENGTH: 20
<212> TYPE: RNA
<213> ORGANISM: Homo sapiens

<400> SEQUENCE: 85
caccccacca gugcaggcug                                                20

<210> SEQ ID NO 86
<211> LENGTH: 18
<212> TYPE: RNA
<213> ORGANISM: Homo sapiens

<400> SEQUENCE: 86
cucccaccgc ugccucca                                                  18

<210> SEQ ID NO 87
<211> LENGTH: 21
<212> TYPE: RNA
<213> ORGANISM: Homo sapiens

<400> SEQUENCE: 87
cacgcaccug uagucucagc u                                              21

<210> SEQ ID NO 88
<211> LENGTH: 22
<212> TYPE: RNA
<213> ORGANISM: Homo sapiens

<400> SEQUENCE: 88
guccauuuua cagagcgcug au                                             22

<210> SEQ ID NO 89
<211> LENGTH: 21
<212> TYPE: RNA
<213> ORGANISM: Homo sapiens

<400> SEQUENCE: 89
cccgcaccug uagucucagc u                                              21

<210> SEQ ID NO 90
<211> LENGTH: 23
<212> TYPE: RNA
<213> ORGANISM: Homo sapiens

<400> SEQUENCE: 90
aucccagguc aaggcugcag uga                                            23

<210> SEQ ID NO 91
<211> LENGTH: 22
<212> TYPE: RNA
<213> ORGANISM: Homo sapiens

<400> SEQUENCE: 91
uuuggggauu cuaagaggaa ga                                             22

<210> SEQ ID NO 92
<211> LENGTH: 23
<212> TYPE: RNA
<213> ORGANISM: Homo sapiens -continued

```
<400> SEQUENCE: 92
guagucgugg ccgagugguu aag                                         23

<210> SEQ ID NO 93
<211> LENGTH: 21
<212> TYPE: RNA
<213> ORGANISM: Homo sapiens

<400> SEQUENCE: 93
ccugggcaac agagcgagac u                                           21

<210> SEQ ID NO 94
<211> LENGTH: 18
<212> TYPE: RNA
<213> ORGANISM: Homo sapiens

<400> SEQUENCE: 94
aucccaccuc ugcuacca                                               18

<210> SEQ ID NO 95
<211> LENGTH: 21
<212> TYPE: RNA
<213> ORGANISM: Homo sapiens

<400> SEQUENCE: 95
agaccuacuu aucuaccaac a                                           21

<210> SEQ ID NO 96
<211> LENGTH: 21
<212> TYPE: RNA
<213> ORGANISM: Homo sapiens

<400> SEQUENCE: 96
uccccaaccc cugcccgcag a                                           21

<210> SEQ ID NO 97
<211> LENGTH: 20
<212> TYPE: RNA
<213> ORGANISM: Homo sapiens

<400> SEQUENCE: 97
uauccgcugg cuuacucucu                                             20

<210> SEQ ID NO 98
<211> LENGTH: 22
<212> TYPE: RNA
<213> ORGANISM: Homo sapiens

<400> SEQUENCE: 98
cugcagacuc gaccucccag gc                                          22

<210> SEQ ID NO 99
<211> LENGTH: 19
<212> TYPE: RNA
<213> ORGANISM: Homo sapiens

<400> SEQUENCE: 99
guuugggccu gguuaguac                                              19

<210> SEQ ID NO 100
<211> LENGTH: 26
<212> TYPE: RNA
```

<213> ORGANISM: Homo sapiens

<400> SEQUENCE: 100
ggcucguugg ucuagggua ugauuc                                          26

<210> SEQ ID NO 101
<211> LENGTH: 22
<212> TYPE: RNA
<213> ORGANISM: Homo sapiens

<400> SEQUENCE: 101
ucagaaccga ccgccuccca gc                                             22

<210> SEQ ID NO 102
<211> LENGTH: 22
<212> TYPE: RNA
<213> ORGANISM: Homo sapiens

<400> SEQUENCE: 102
aacccggccc uccuugucca ca                                             22

<210> SEQ ID NO 103
<211> LENGTH: 22
<212> TYPE: RNA
<213> ORGANISM: Homo sapiens

<400> SEQUENCE: 103
ccccgcgcag guucgaaucc ug                                             22

<210> SEQ ID NO 104
<211> LENGTH: 22
<212> TYPE: RNA
<213> ORGANISM: Homo sapiens

<400> SEQUENCE: 104
aagccucugu ccccaccca gg                                              22

<210> SEQ ID NO 105
<211> LENGTH: 18
<212> TYPE: RNA
<213> ORGANISM: Homo sapiens

<400> SEQUENCE: 105 gucggucug augguagu                                                   18

<210> SEQ ID NO 106
<211> LENGTH: 21
<212> TYPE: RNA
<213> ORGANISM: Homo sapiens

<400> SEQUENCE: 106
cugcacucca gccugggcga c                                              21

<210> SEQ ID NO 107
<211> LENGTH: 21
<212> TYPE: RNA
<213> ORGANISM: Homo sapiens

<400> SEQUENCE: 107
agcucugucu gugucucuag g                                              21

<210> SEQ ID NO 108
<211> LENGTH: 23

<212> TYPE: RNA
<213> ORGANISM: Homo sapiens

<400> SEQUENCE: 108
cccugggguu cugaggacau gcu                                           23

<210> SEQ ID NO 109
<211> LENGTH: 20
<212> TYPE: RNA
<213> ORGANISM: Homo sapiens

<400> SEQUENCE: 109
aaaaguaauc gcacuuuuug                                               20

<210> SEQ ID NO 110
<211> LENGTH: 20
<212> TYPE: RNA
<213> ORGANISM: Homo sapiens

<400> SEQUENCE: 110
aaaaguaauc gcagguuuug                                               20

<210> SEQ ID NO 111
<211> LENGTH: 20
<212> TYPE: RNA
<213> ORGANISM: Homo sapiens

<400> SEQUENCE: 111
aaaaguaaug gcaguuuuug                                               20

<210> SEQ ID NO 112
<211> LENGTH: 20
<212> TYPE: RNA
<213> ORGANISM: Homo sapiens

<400> SEQUENCE: 112
aaaaguaauc guaguuuuug                                               20

<210> SEQ ID NO 113
<211> LENGTH: 22
<212> TYPE: RNA
<213> ORGANISM: Homo sapiens

<400> SEQUENCE: 113
ccgcccucug uaccucccca ga                                            22

<210> SEQ ID NO 114
<211> LENGTH: 19
<212> TYPE: RNA
<213> ORGANISM: Homo sapiens

<400> SEQUENCE: 114
uuuagugagg cccucggau                                                19

<210> SEQ ID NO 115
<211> LENGTH: 18
<212> TYPE: RNA
<213> ORGANISM: Homo sapiens

<400> SEQUENCE: 115
ggcggcggcg gcggcggc                                                 18

<210> SEQ ID NO 116

```
<211> LENGTH: 20
<212> TYPE: RNA
<213> ORGANISM: Homo sapiens

<400> SEQUENCE: 116
cucccucuga gccugccgcc                                                    20

<210> SEQ ID NO 117
<211> LENGTH: 22
<212> TYPE: RNA
<213> ORGANISM: Homo sapiens

<400> SEQUENCE: 117
cacugcacuc cagccugggu ga                                                 22

<210> SEQ ID NO 118
<211> LENGTH: 21
<212> TYPE: RNA
<213> ORGANISM: Homo sapiens

<400> SEQUENCE: 118
uugaggucgg acaugguggc u                                                  21

<210> SEQ ID NO 119
<211> LENGTH: 22
<212> TYPE: RNA
<213> ORGANISM: Homo sapiens

<400> SEQUENCE: 119
cacugcacuc cagccugggc aa                                                 22

<210> SEQ ID NO 120
<211> LENGTH: 21
<212> TYPE: RNA
<213> ORGANISM: Homo sapiens

<400> SEQUENCE: 120
cccaggacag uuucagugau g                                                  21

<210> SEQ ID NO 121
<211> LENGTH: 21
<212> TYPE: RNA
<213> ORGANISM: Homo sapiens

<400> SEQUENCE: 121
acugcacucc agccugggca a                                                  21

<210> SEQ ID NO 122
<211> LENGTH: 22
<212> TYPE: RNA
<213> ORGANISM: Homo sapiens

<400> SEQUENCE: 122
ccuccucaca ccucuccugg ca                                                 22

<210> SEQ ID NO 123
<211> LENGTH: 22
<212> TYPE: RNA
<213> ORGANISM: Homo sapiens

<400> SEQUENCE: 123
cucggccuuu gcucgcagca cu                                                 22
```

-continued

```
<210> SEQ ID NO 124
<211> LENGTH: 21
<212> TYPE: RNA
<213> ORGANISM: Homo sapiens

<400> SEQUENCE: 124
acgccccuuc ugauucugcc u                                              21

<210> SEQ ID NO 125
<211> LENGTH: 20
<212> TYPE: RNA
<213> ORGANISM: Homo sapiens

<400> SEQUENCE: 125
cugcacucca gccugggcga                                                20

<210> SEQ ID NO 126
<211> LENGTH: 21
<212> TYPE: RNA
<213> ORGANISM: Homo sapiens

<400> SEQUENCE: 126
cacugcacuc cagccugggc a                                              21

<210> SEQ ID NO 127
<211> LENGTH: 23
<212> TYPE: RNA
<213> ORGANISM: Homo sapiens

<400> SEQUENCE: 127
acugcaaccu ccaccuccug ggu                                            23

<210> SEQ ID NO 128
<211> LENGTH: 22
<212> TYPE: RNA
<213> ORGANISM: Homo sapiens

<400> SEQUENCE: 128
cucccuuccu gccccucaga ga                                             22

<210> SEQ ID NO 129
<211> LENGTH: 21
<212> TYPE: RNA
<213> ORGANISM: Homo sapiens

<400> SEQUENCE: 129
cacugcacuc cagccugggu a                                              21

<210> SEQ ID NO 130
<211> LENGTH: 21
<212> TYPE: RNA
<213> ORGANISM: Homo sapiens

<400> SEQUENCE: 130
cccgccuguc ucucucuugc a                                              21

<210> SEQ ID NO 131
<211> LENGTH: 23
<212> TYPE: RNA
<213> ORGANISM: Homo sapiens

<400> SEQUENCE: 131
ccugaccccc augucgccuc ugu                                            23
```

```
<210> SEQ ID NO 132
<211> LENGTH: 22
<212> TYPE: RNA
<213> ORGANISM: Homo sapiens

<400> SEQUENCE: 132
uuggugagga ccccaagcuc gg                                          22

<210> SEQ ID NO 133
<211> LENGTH: 21
<212> TYPE: RNA
<213> ORGANISM: Homo sapiens

<400> SEQUENCE: 133
ucccugucac cucuggaccu g                                           21

<210> SEQ ID NO 134
<211> LENGTH: 21
<212> TYPE: RNA
<213> ORGANISM: Homo sapiens

<400> SEQUENCE: 134 cccccccggag cggcccugag a                                          21

<210> SEQ ID NO 135
<211> LENGTH: 18
<212> TYPE: RNA
<213> ORGANISM: Homo sapiens

<400> SEQUENCE: 135
aucugaguca cggcacca                                               18

<210> SEQ ID NO 136
<211> LENGTH: 19
<212> TYPE: RNA
<213> ORGANISM: Homo sapiens

<400> SEQUENCE: 136
uuuagugagg cccucugau                                              19

<210> SEQ ID NO 137
<211> LENGTH: 21
<212> TYPE: RNA
<213> ORGANISM: Homo sapiens

<400> SEQUENCE: 137
aggcguucug ggcuguagug c                                           21

<210> SEQ ID NO 138
<211> LENGTH: 25
<212> TYPE: RNA
<213> ORGANISM: Homo sapiens

<400> SEQUENCE: 138
gaagcagcgc cugucgcaac ucgcc                                       25

<210> SEQ ID NO 139
<211> LENGTH: 25
<212> TYPE: RNA
<213> ORGANISM: Homo sapiens

<400> SEQUENCE: 139
ucuagauagu caaguucuga uccag                                       25
```

```
<210> SEQ ID NO 140
<211> LENGTH: 21
<212> TYPE: RNA
<213> ORGANISM: Homo sapiens

<400> SEQUENCE: 140
aaagacuucc uucucucgcc u                                              21

<210> SEQ ID NO 141
<211> LENGTH: 22
<212> TYPE: RNA
<213> ORGANISM: Homo sapiens

<400> SEQUENCE: 141
ucacaccugu aaucccagca cu                                             22

<210> SEQ ID NO 142
<211> LENGTH: 22
<212> TYPE: RNA
<213> ORGANISM: Homo sapiens

<400> SEQUENCE: 142
ucucacucug uugcccaggc ug                                             22

<210> SEQ ID NO 143
<211> LENGTH: 19
<212> TYPE: RNA
<213> ORGANISM: Homo sapiens

<400> SEQUENCE: 143
agcagggugg ggccugguu                                                 19

<210> SEQ ID NO 144
<211> LENGTH: 23
<212> TYPE: RNA
<213> ORGANISM: Homo sapiens

<400> SEQUENCE: 144
aguugccagg gcugccuuug gug                                            23

<210> SEQ ID NO 145
<211> LENGTH: 22
<212> TYPE: RNA
<213> ORGANISM: Homo sapiens

<400> SEQUENCE: 145
cucuccgcca ccuccaccgc gg                                             22

<210> SEQ ID NO 146
<211> LENGTH: 22
<212> TYPE: RNA
<213> ORGANISM: Homo sapiens

<400> SEQUENCE: 146
gccgccauua cuuuugcacc aa                                             22

<210> SEQ ID NO 147
<211> LENGTH: 21
<212> TYPE: RNA
<213> ORGANISM: Homo sapiens

<400> SEQUENCE: 147
```
ucuccccgcg cagguucgaa u                                        21

<210> SEQ ID NO 148
<211> LENGTH: 20
<212> TYPE: RNA
<213> ORGANISM: Homo sapiens

<400> SEQUENCE: 148
cacugcacuc cagccuggcu                                          20

<210> SEQ ID NO 149
<211> LENGTH: 21
<212> TYPE: RNA
<213> ORGANISM: Homo sapiens

<400> SEQUENCE: 149
cugcacucca gcuugggcaa c                                        21

<210> SEQ ID NO 150
<211> LENGTH: 21
<212> TYPE: RNA
<213> ORGANISM: Homo sapiens

<400> SEQUENCE: 150
caugccacug cacuccagcc u                                        21

<210> SEQ ID NO 151
<211> LENGTH: 23
<212> TYPE: RNA
<213> ORGANISM: Homo sapiens

<400> SEQUENCE: 151
ucccggaccc agcccucagg acu                                      23

<210> SEQ ID NO 152
<211> LENGTH: 20
<212> TYPE: RNA
<213> ORGANISM: Homo sapiens

<400> SEQUENCE: 152
caaaaccgcg auuacucuug                                          20

<210> SEQ ID NO 153
<211> LENGTH: 22
<212> TYPE: RNA
<213> ORGANISM: Homo sapiens

<400> SEQUENCE: 153
cggcggcucc agggaccugg cg                                       22

<210> SEQ ID NO 154
<211> LENGTH: 20
<212> TYPE: RNA
<213> ORGANISM: Homo sapiens

<400> SEQUENCE: 154
ugcacgcgac cauagagccu                                          20

<210> SEQ ID NO 155
<211> LENGTH: 21
<212> TYPE: RNA
<213> ORGANISM: Homo sapiens

<400> SEQUENCE: 155
cacccaggcu ggagugcagu g                                      21

<210> SEQ ID NO 156
<211> LENGTH: 20
<212> TYPE: RNA
<213> ORGANISM: Homo sapiens

<400> SEQUENCE: 156
accucggaag cuaagcaggg                                        20

<210> SEQ ID NO 157
<211> LENGTH: 22
<212> TYPE: RNA
<213> ORGANISM: Homo sapiens

<400> SEQUENCE: 157
uaacggacag auacggggca ga                                     22

<210> SEQ ID NO 158
<211> LENGTH: 22
<212> TYPE: RNA
<213> ORGANISM: Homo sapiens

<400> SEQUENCE: 158
agcggaacuu gaggagccga ga                                     22

<210> SEQ ID NO 159
<211> LENGTH: 23
<212> TYPE: RNA
<213> ORGANISM: Homo sapiens

<400> SEQUENCE: 159
gagaggaaca ugggcucagg aca                                    23

<210> SEQ ID NO 160
<211> LENGTH: 20
<212> TYPE: RNA
<213> ORGANISM: Homo sapiens

<400> SEQUENCE: 160
cuugagacuc ugggucaguc                                        20

<210> SEQ ID NO 161
<211> LENGTH: 20
<212> TYPE: RNA
<213> ORGANISM: Homo sapiens

<400> SEQUENCE: 161
cagcggcugc gcaucucggg                                        20

<210> SEQ ID NO 162
<211> LENGTH: 22
<212> TYPE: RNA
<213> ORGANISM: Homo sapiens

<400> SEQUENCE: 162
aggcauuaga uucucauaag ga                                     22

<210> SEQ ID NO 163
<211> LENGTH: 28
<212> TYPE: RNA
<213> ORGANISM: Homo sapiens

<400> SEQUENCE: 163
uuuccuucuc cacucccacu gccucacu                                          28

<210> SEQ ID NO 164
<211> LENGTH: 20
<212> TYPE: RNA
<213> ORGANISM: Homo sapiens

<400> SEQUENCE: 164
cuuagagacg gggucuugcu                                                   20

<210> SEQ ID NO 165
<211> LENGTH: 21
<212> TYPE: RNA
<213> ORGANISM: Homo sapiens

<400> SEQUENCE: 165
ugguccaacg acaggaguag g                                                 21

<210> SEQ ID NO 166
<211> LENGTH: 21
<212> TYPE: RNA
<213> ORGANISM: Homo sapiens

<400> SEQUENCE: 166
cacugcgcuc cagccugggc a                                                 21

<210> SEQ ID NO 167
<211> LENGTH: 22
<212> TYPE: RNA
<213> ORGANISM: Homo sapiens

<400> SEQUENCE: 167
ucuucaccug ccucugccug ca                                                22

<210> SEQ ID NO 168
<211> LENGTH: 20
<212> TYPE: RNA
<213> ORGANISM: Homo sapiens

<400> SEQUENCE: 168
aggcccuguc cucugcccca                                                   20

<210> SEQ ID NO 169
<211> LENGTH: 20
<212> TYPE: RNA
<213> ORGANISM: Homo sapiens

<400> SEQUENCE: 169
cuggcugcuu cccuuggucu                                                   20

<210> SEQ ID NO 170
<211> LENGTH: 19
<212> TYPE: RNA
<213> ORGANISM: Homo sapiens

<400> SEQUENCE: 170
uggcccaaga ccucagacc                                                    19

<210> SEQ ID NO 171
<211> LENGTH: 31
<212> TYPE: RNA
<213> ORGANISM: Homo sapiens

```
<400> SEQUENCE: 171
gugccuguag ucccagcuac ucaggaggcu g                                    31

<210> SEQ ID NO 172
<211> LENGTH: 23
<212> TYPE: RNA
<213> ORGANISM: Homo sapiens

<400> SEQUENCE: 172
ugcgcguccc gcccggucug gga                                             23

<210> SEQ ID NO 173
<211> LENGTH: 20
<212> TYPE: RNA
<213> ORGANISM: Homo sapiens

<400> SEQUENCE: 173
uuuagagacg gggacuugcu                                                 20

<210> SEQ ID NO 174
<211> LENGTH: 22
<212> TYPE: RNA
<213> ORGANISM: Homo sapiens

<400> SEQUENCE: 174
aucccuuuau cuguccucua gg                                              22

<210> SEQ ID NO 175
<211> LENGTH: 22
<212> TYPE: RNA
<213> ORGANISM: Homo sapiens

<400> SEQUENCE: 175
cacugcauuc cagccugggc ga                                              22

<210> SEQ ID NO 176
<211> LENGTH: 21
<212> TYPE: RNA
<213> ORGANISM: Homo sapiens

<400> SEQUENCE: 176
uucccucacu cuucucucag g                                               21

<210> SEQ ID NO 177
<211> LENGTH: 21
<212> TYPE: RNA
<213> ORGANISM: Homo sapiens

<400> SEQUENCE: 177
uccucuuaga auccccaaac c                                               21

<210> SEQ ID NO 178
<211> LENGTH: 21
<212> TYPE: RNA
<213> ORGANISM: Homo sapiens

<400> SEQUENCE: 178
ccucggccgc uuucgaagcc a                                               21

<210> SEQ ID NO 179
<211> LENGTH: 21
<212> TYPE: RNA
```

<213> ORGANISM: Homo sapiens

<400> SEQUENCE: 179
caugguccau uuugcucugc u                                              21

<210> SEQ ID NO 180
<211> LENGTH: 18
<212> TYPE: RNA
<213> ORGANISM: Homo sapiens

<400> SEQUENCE: 180
uugcccaggc uggagugc                                                  18

<210> SEQ ID NO 181
<211> LENGTH: 23
<212> TYPE: RNA
<213> ORGANISM: Homo sapiens

<400> SEQUENCE: 181
ucguagcccc uccgccguuu gca                                            23

<210> SEQ ID NO 182
<211> LENGTH: 21
<212> TYPE: RNA
<213> ORGANISM: Homo sapiens

<400> SEQUENCE: 182
acccaggcug gagugcagug g                                              21

<210> SEQ ID NO 183
<211> LENGTH: 18
<212> TYPE: RNA
<213> ORGANISM: Homo sapiens

<400> SEQUENCE: 183
aaauacugau acagugcu                                                  18

<210> SEQ ID NO 184
<211> LENGTH: 22
<212> TYPE: RNA
<213> ORGANISM: Homo sapiens

<400> SEQUENCE: 184
ucugacucuc cgccucuccc ca                                             22

<210> SEQ ID NO 185
<211> LENGTH: 21
<212> TYPE: RNA
<213> ORGANISM: Homo sapiens

<400> SEQUENCE: 185
caccuccacu guccacacuu g                                              21

<210> SEQ ID NO 186
<211> LENGTH: 20
<212> TYPE: RNA
<213> ORGANISM: Homo sapiens

<400> SEQUENCE: 186
ucugcagguc ucuggugccu                                                20

<210> SEQ ID NO 187
<211> LENGTH: 21

<212> TYPE: RNA
<213> ORGANISM: Homo sapiens

<400> SEQUENCE: 187
cccccuuucc cugagccugc a					21

<210> SEQ ID NO 188
<211> LENGTH: 22
<212> TYPE: RNA
<213> ORGANISM: Homo sapiens

<400> SEQUENCE: 188
acugccuuuu gaugaccggg ac					22

<210> SEQ ID NO 189
<211> LENGTH: 22
<212> TYPE: RNA
<213> ORGANISM: Homo sapiens

<400> SEQUENCE: 189
auucgcuggg aauucagccu cu					22

<210> SEQ ID NO 190
<211> LENGTH: 21
<212> TYPE: RNA
<213> ORGANISM: Homo sapiens

<400> SEQUENCE: 190
uuccacugcc acuaccuaau u					21

<210> SEQ ID NO 191
<211> LENGTH: 18
<212> TYPE: RNA
<213> ORGANISM: Homo sapiens

<400> SEQUENCE: 191
uccugugcug agcugcug					18

<210> SEQ ID NO 192
<211> LENGTH: 21
<212> TYPE: RNA
<213> ORGANISM: Homo sapiens

<400> SEQUENCE: 192
ccuaugagaa ucuaaugccu c					21

<210> SEQ ID NO 193
<211> LENGTH: 24
<212> TYPE: RNA
<213> ORGANISM: Homo sapiens

<400> SEQUENCE: 193
ccccggaggu ugaagcuaca guga					24

<210> SEQ ID NO 194
<211> LENGTH: 22
<212> TYPE: RNA
<213> ORGANISM: Homo sapiens

<400> SEQUENCE: 194
aaaaaccgug auuacuuuug ca					22

<210> SEQ ID NO 195

```
<211> LENGTH: 22
<212> TYPE: RNA
<213> ORGANISM: Homo sapiens

<400> SEQUENCE: 195
uuauccucca guagacuagg ga                                              22

<210> SEQ ID NO 196
<211> LENGTH: 21
<212> TYPE: RNA
<213> ORGANISM: Homo sapiens

<400> SEQUENCE: 196
gaacucaccc ucugcuccca g                                               21

<210> SEQ ID NO 197
<211> LENGTH: 20
<212> TYPE: RNA
<213> ORGANISM: Homo sapiens

<400> SEQUENCE: 197
ugacagagcg agaccuuguc                                                 20

<210> SEQ ID NO 198
<211> LENGTH: 21
<212> TYPE: RNA
<213> ORGANISM: Homo sapiens

<400> SEQUENCE: 198
ccuggcggcu gugucuucac a                                               21

<210> SEQ ID NO 199
<211> LENGTH: 23
<212> TYPE: RNA
<213> ORGANISM: Homo sapiens

<400> SEQUENCE: 199
ugagccggcu gagcaggaag cgg                                             23

<210> SEQ ID NO 200
<211> LENGTH: 22
<212> TYPE: RNA
<213> ORGANISM: Homo sapiens

<400> SEQUENCE: 200
ucaguccagu caucucccuu ca                                              22

<210> SEQ ID NO 201
<211> LENGTH: 20
<212> TYPE: RNA
<213> ORGANISM: Homo sapiens

<400> SEQUENCE: 201
cugggugaca gagcgagacc                                                 20

<210> SEQ ID NO 202
<211> LENGTH: 19
<212> TYPE: RNA
<213> ORGANISM: Homo sapiens

<400> SEQUENCE: 202
ggcggcggag gcggcggug                                                  19
```

```
<210> SEQ ID NO 203
<211> LENGTH: 21
<212> TYPE: RNA
<213> ORGANISM: Homo sapiens

<400> SEQUENCE: 203
cucacaccug uaaucccagc a                                              21

<210> SEQ ID NO 204
<211> LENGTH: 21
<212> TYPE: RNA
<213> ORGANISM: Homo sapiens

<400> SEQUENCE: 204
ccucuuccuc cagccucuga a                                              21

<210> SEQ ID NO 205
<211> LENGTH: 23
<212> TYPE: RNA
<213> ORGANISM: Homo sapiens

<400> SEQUENCE: 205
acugcaaccu cugacgccug ggu                                            23

<210> SEQ ID NO 206
<211> LENGTH: 18
<212> TYPE: RNA
<213> ORGANISM: Homo sapiens

<400> SEQUENCE: 206
cacccugaac gcgccggc                                                  18

<210> SEQ ID NO 207
<211> LENGTH: 21
<212> TYPE: RNA
<213> ORGANISM: Homo sapiens

<400> SEQUENCE: 207
ucaggaguuu gagaccagcc u                                              21

<210> SEQ ID NO 208
<211> LENGTH: 22
<212> TYPE: RNA
<213> ORGANISM: Homo sapiens

<400> SEQUENCE: 208
cacccaggcu ggaaugcagu gg                                             22

<210> SEQ ID NO 209
<211> LENGTH: 21
<212> TYPE: RNA
<213> ORGANISM: Homo sapiens

<400> SEQUENCE: 209
ccccugggcu guuacuguuc c                                              21

<210> SEQ ID NO 210
<211> LENGTH: 21
<212> TYPE: RNA
<213> ORGANISM: Homo sapiens

<400> SEQUENCE: 210
ccagcugccu cuccuccauc g                                              21
```

```
<210> SEQ ID NO 211
<211> LENGTH: 22
<212> TYPE: RNA
<213> ORGANISM: Homo sapiens

<400> SEQUENCE: 211
aaaaacugca auuccuuug ca                                              22

<210> SEQ ID NO 212
<211> LENGTH: 21
<212> TYPE: RNA
<213> ORGANISM: Homo sapiens

<400> SEQUENCE: 212
uagaacacuc uggccccauc u                                              21

<210> SEQ ID NO 213
<211> LENGTH: 20
<212> TYPE: RNA
<213> ORGANISM: Homo sapiens

<400> SEQUENCE: 213
acccuggccu ccacucugcc                                                20

<210> SEQ ID NO 214
<211> LENGTH: 22
<212> TYPE: RNA
<213> ORGANISM: Homo sapiens

<400> SEQUENCE: 214
ucaggcuuug caucccggga cg                                             22

<210> SEQ ID NO 215
<211> LENGTH: 18
<212> TYPE: RNA
<213> ORGANISM: Homo sapiens

<400> SEQUENCE: 215
aggaggagga ggaggacg                                                  18

<210> SEQ ID NO 216
<211> LENGTH: 20
<212> TYPE: RNA
<213> ORGANISM: Homo sapiens

<400> SEQUENCE: 216
aaaaguaauu gugguuuuug                                                20

<210> SEQ ID NO 217
<211> LENGTH: 26
<212> TYPE: RNA
<213> ORGANISM: Homo sapiens

<400> SEQUENCE: 217
uggauaugau gacugauuac cugaga                                         26

<210> SEQ ID NO 218
<211> LENGTH: 22
<212> TYPE: RNA
<213> ORGANISM: Homo sapiens

<400> SEQUENCE: 218
uuagaggcug gaauagagau uc                                             22
```

```
<210> SEQ ID NO 219
<211> LENGTH: 22
<212> TYPE: RNA
<213> ORGANISM: Homo sapiens

<400> SEQUENCE: 219
cccauguccu gucuccuuuu gg                                                22

<210> SEQ ID NO 220
<211> LENGTH: 21
<212> TYPE: RNA
<213> ORGANISM: Homo sapiens

<400> SEQUENCE: 220
aggcuccaug accccggcag g                                                 21

<210> SEQ ID NO 221
<211> LENGTH: 22
<212> TYPE: RNA
<213> ORGANISM: Homo sapiens

<400> SEQUENCE: 221
auguugacuc uccuaccugg gc                                                22

<210> SEQ ID NO 222
<211> LENGTH: 20
<212> TYPE: RNA
<213> ORGANISM: Homo sapiens

<400> SEQUENCE: 222
ugagaggcag agguugcagu                                                   20

<210> SEQ ID NO 223
<211> LENGTH: 20
<212> TYPE: RNA
<213> ORGANISM: Homo sapiens

<400> SEQUENCE: 223
uuacugaggg gaugaaggau                                                   20

<210> SEQ ID NO 224
<211> LENGTH: 21
<212> TYPE: RNA
<213> ORGANISM: Homo sapiens

<400> SEQUENCE: 224
cuuuggggau ucuaagaguu a                                                 21

<210> SEQ ID NO 225
<211> LENGTH: 21
<212> TYPE: RNA
<213> ORGANISM: Homo sapiens

<400> SEQUENCE: 225
agacugaccu ucaaccccac a                                                 21

<210> SEQ ID NO 226
<211> LENGTH: 20
<212> TYPE: RNA
<213> ORGANISM: Homo sapiens

<400> SEQUENCE: 226
```
uugcaaagga auccugggcc                                                   20

<210> SEQ ID NO 227
<211> LENGTH: 19
<212> TYPE: RNA
<213> ORGANISM: Homo sapiens

<400> SEQUENCE: 227
ucgacacuuc gaacgcaau                                                    19

<210> SEQ ID NO 228
<211> LENGTH: 21
<212> TYPE: RNA
<213> ORGANISM: Homo sapiens

<400> SEQUENCE: 228
cuuccaucuc caucaccuug a                                                 21

<210> SEQ ID NO 229
<211> LENGTH: 22
<212> TYPE: RNA
<213> ORGANISM: Homo sapiens

<400> SEQUENCE: 229
ucuucaggaa cucuggcuaa cu                                                22

<210> SEQ ID NO 230
<211> LENGTH: 20
<212> TYPE: RNA
<213> ORGANISM: Homo sapiens

<400> SEQUENCE: 230
cacugcagac ucccugggcu                                                   20

<210> SEQ ID NO 231
<211> LENGTH: 21
<212> TYPE: RNA
<213> ORGANISM: Homo sapiens

<400> SEQUENCE: 231
agaguugcug ccgcugcugu c                                                 21

<210> SEQ ID NO 232
<211> LENGTH: 22
<212> TYPE: RNA
<213> ORGANISM: Homo sapiens

<400> SEQUENCE: 232
uugaggggag aaugaggugg ag                                                22

<210> SEQ ID NO 233
<211> LENGTH: 19
<212> TYPE: RNA
<213> ORGANISM: Homo sapiens

<400> SEQUENCE: 233
accugugcuu ccucuuuga                                                    19

<210> SEQ ID NO 234
<211> LENGTH: 21
<212> TYPE: RNA
<213> ORGANISM: Homo sapiens

<400> SEQUENCE: 234 agcgagggu ccgccggcca c                               21

<210> SEQ ID NO 235
<211> LENGTH: 22
<212> TYPE: RNA
<213> ORGANISM: Homo sapiens

<400> SEQUENCE: 235
ugucuugcuc uguugcccag gu                             22

<210> SEQ ID NO 236
<211> LENGTH: 23
<212> TYPE: RNA
<213> ORGANISM: Homo sapiens

<400> SEQUENCE: 236
cuggcugugg guuccuuauc ugu                            23

<210> SEQ ID NO 237
<211> LENGTH: 22
<212> TYPE: RNA
<213> ORGANISM: Homo sapiens

<400> SEQUENCE: 237
aaaaguaauu gugguuucug cc                             22

<210> SEQ ID NO 238
<211> LENGTH: 21
<212> TYPE: RNA
<213> ORGANISM: Homo sapiens

<400> SEQUENCE: 238
ucugcagccc uggagccccc u                              21

<210> SEQ ID NO 239
<211> LENGTH: 21
<212> TYPE: RNA
<213> ORGANISM: Homo sapiens

<400> SEQUENCE: 239
aaaagcuguc cacuguagag u                              21

<210> SEQ ID NO 240
<211> LENGTH: 20
<212> TYPE: RNA
<213> ORGANISM: Homo sapiens

<400> SEQUENCE: 240
guucccucca ccucucagca                                20

<210> SEQ ID NO 241
<211> LENGTH: 22
<212> TYPE: RNA
<213> ORGANISM: Homo sapiens

<400> SEQUENCE: 241
ugacuucuua uucuuuccug ug                             22

<210> SEQ ID NO 242
<211> LENGTH: 22
<212> TYPE: RNA
<213> ORGANISM: Homo sapiens

```
<400> SEQUENCE: 242
auggcccugu gucuccucgg ag                                          22

<210> SEQ ID NO 243
<211> LENGTH: 23
<212> TYPE: RNA
<213> ORGANISM: Homo sapiens

<400> SEQUENCE: 243
ccucuucuca gaacacuucc ugg                                         23

<210> SEQ ID NO 244
<211> LENGTH: 23
<212> TYPE: RNA
<213> ORGANISM: Homo sapiens

<400> SEQUENCE: 244
cccaccucgg ccucccaaag ugc                                         23

<210> SEQ ID NO 245
<211> LENGTH: 21
<212> TYPE: RNA
<213> ORGANISM: Homo sapiens

<400> SEQUENCE: 245
cuguucucug cucucccgc a                                            21

<210> SEQ ID NO 246
<211> LENGTH: 25
<212> TYPE: RNA
<213> ORGANISM: Homo sapiens

<400> SEQUENCE: 246 acugggagg acagccauga cagga                                        25

<210> SEQ ID NO 247
<211> LENGTH: 23
<212> TYPE: RNA
<213> ORGANISM: Homo sapiens

<400> SEQUENCE: 247
acuucacccu cugccucccg ggu                                         23

<210> SEQ ID NO 248
<211> LENGTH: 18
<212> TYPE: RNA
<213> ORGANISM: Homo sapiens

<400> SEQUENCE: 248
cccuccucuc cuguggcc                                               18

<210> SEQ ID NO 249
<211> LENGTH: 21
<212> TYPE: RNA
<213> ORGANISM: Homo sapiens

<400> SEQUENCE: 249
ucuguauugu gaauggggga a                                           21

<210> SEQ ID NO 250
<211> LENGTH: 19
<212> TYPE: RNA
<213> ORGANISM: Homo sapiens
```

```
<400> SEQUENCE: 250
cccaggcugg agugcagug                                              19

<210> SEQ ID NO 251
<211> LENGTH: 19
<212> TYPE: RNA
<213> ORGANISM: Homo sapiens

<400> SEQUENCE: 251 uguguccccca gugucuguu                                             19

<210> SEQ ID NO 252
<211> LENGTH: 18
<212> TYPE: RNA
<213> ORGANISM: Homo sapiens

<400> SEQUENCE: 252
cccaggcugg agugcagu                                               18

<210> SEQ ID NO 253
<211> LENGTH: 22
<212> TYPE: RNA
<213> ORGANISM: Homo sapiens

<400> SEQUENCE: 253
ugaccagcuc ucauccccag cg                                          22

<210> SEQ ID NO 254
<211> LENGTH: 22
<212> TYPE: RNA
<213> ORGANISM: Homo sapiens

<400> SEQUENCE: 254
ucccaaagau ugauaagcug ug                                          22

<210> SEQ ID NO 255
<211> LENGTH: 23
<212> TYPE: RNA
<213> ORGANISM: Homo sapiens

<400> SEQUENCE: 255
uugggaagaa uucugauauu ggu                                         23

<210> SEQ ID NO 256
<211> LENGTH: 20
<212> TYPE: RNA
<213> ORGANISM: Homo sapiens

<400> SEQUENCE: 256
gaccacacuc cauccugggc                                             20

<210> SEQ ID NO 257
<211> LENGTH: 20
<212> TYPE: RNA
<213> ORGANISM: Homo sapiens

<400> SEQUENCE: 257
gugugugcac cugugucugu                                             20

<210> SEQ ID NO 258
<211> LENGTH: 23
<212> TYPE: RNA
```

```
<213> ORGANISM: Homo sapiens

<400> SEQUENCE: 258
uccccaaacc uugucuggac aug                                          23

<210> SEQ ID NO 259
<211> LENGTH: 20
<212> TYPE: RNA
<213> ORGANISM: Homo sapiens

<400> SEQUENCE: 259
ugcugccgcu gcuguugcuc                                              20

<210> SEQ ID NO 260
<211> LENGTH: 22
<212> TYPE: RNA
<213> ORGANISM: Homo sapiens

<400> SEQUENCE: 260
cucaaccuca aaacggcccu cc                                           22

<210> SEQ ID NO 261
<211> LENGTH: 21
<212> TYPE: RNA
<213> ORGANISM: Homo sapiens

<400> SEQUENCE: 261
gagcccggga ggcagagguu g                                            21

<210> SEQ ID NO 262
<211> LENGTH: 21
<212> TYPE: RNA
<213> ORGANISM: Homo sapiens

<400> SEQUENCE: 262
uggggcccag gaaucugcau u                                            21

<210> SEQ ID NO 263
<211> LENGTH: 23
<212> TYPE: RNA
<213> ORGANISM: Homo sapiens

<400> SEQUENCE: 263
uccaaucaca cuucguugcc uga                                          23

<210> SEQ ID NO 264
<211> LENGTH: 19
<212> TYPE: RNA
<213> ORGANISM: Homo sapiens

<400> SEQUENCE: 264
cucccgggau ccgaagcug                                               19

<210> SEQ ID NO 265
<211> LENGTH: 21
<212> TYPE: RNA
<213> ORGANISM: Homo sapiens

<400> SEQUENCE: 265
uucccucagu uaacuuuccu g                                            21

<210> SEQ ID NO 266
<211> LENGTH: 22
```

```
<212> TYPE: RNA
<213> ORGANISM: Homo sapiens

<400> SEQUENCE: 266
ugcccaggcu gcagugcagu gg                                    22

<210> SEQ ID NO 267
<211> LENGTH: 18
<212> TYPE: RNA
<213> ORGANISM: Homo sapiens

<400> SEQUENCE: 267
aacccaggac gccgagcu                                         18

<210> SEQ ID NO 268
<211> LENGTH: 24
<212> TYPE: RNA
<213> ORGANISM: Homo sapiens

<400> SEQUENCE: 268
caggucucgc uuugucaccc aggc                                  24

<210> SEQ ID NO 269
<211> LENGTH: 22
<212> TYPE: RNA
<213> ORGANISM: Homo sapiens

<400> SEQUENCE: 269
gaagacccga gccugccggg gg                                    22

<210> SEQ ID NO 270
<211> LENGTH: 20
<212> TYPE: RNA
<213> ORGANISM: Homo sapiens

<400> SEQUENCE: 270
uuagggaggc gagauugagc                                       20

<210> SEQ ID NO 271
<211> LENGTH: 21
<212> TYPE: RNA
<213> ORGANISM: Homo sapiens

<400> SEQUENCE: 271
ugacuucugc cuucccagag u                                     21

<210> SEQ ID NO 272
<211> LENGTH: 23
<212> TYPE: RNA
<213> ORGANISM: Homo sapiens

<400> SEQUENCE: 272
agagucgaga gugggagaag agc                                   23

<210> SEQ ID NO 273
<211> LENGTH: 25
<212> TYPE: RNA
<213> ORGANISM: Homo sapiens

<400> SEQUENCE: 273
uggcucagcu ccaauucugc ccacg                                 25

<210> SEQ ID NO 274
```

-continued

```
<211> LENGTH: 23
<212> TYPE: RNA
<213> ORGANISM: Homo sapiens

<400> SEQUENCE: 274
ugcugaaagc cguuucccgu guu                                               23

<210> SEQ ID NO 275
<211> LENGTH: 20
<212> TYPE: RNA
<213> ORGANISM: Homo sapiens

<400> SEQUENCE: 275
ucucauggac uccgcccaca                                                   20

<210> SEQ ID NO 276
<211> LENGTH: 22
<212> TYPE: RNA
<213> ORGANISM: Homo sapiens

<400> SEQUENCE: 276
uggccgagcg cggcucgucg cc                                                22

<210> SEQ ID NO 277
<211> LENGTH: 24
<212> TYPE: RNA
<213> ORGANISM: Homo sapiens

<400> SEQUENCE: 277
cugggagguc aaggcugcag uguc                                              24

<210> SEQ ID NO 278
<211> LENGTH: 20
<212> TYPE: RNA
<213> ORGANISM: Homo sapiens

<400> SEQUENCE: 278
ccuggcgugg acgacuggcc                                                   20

<210> SEQ ID NO 279
<211> LENGTH: 24
<212> TYPE: RNA
<213> ORGANISM: Homo sapiens

<400> SEQUENCE: 279
ccggccucgc gagcgucgcg cagu                                              24

<210> SEQ ID NO 280
<211> LENGTH: 21
<212> TYPE: RNA
<213> ORGANISM: Homo sapiens

<400> SEQUENCE: 280
cucugcccuu ggccucccca g                                                 21

<210> SEQ ID NO 281
<211> LENGTH: 22
<212> TYPE: RNA
<213> ORGANISM: Homo sapiens

<400> SEQUENCE: 281
cgccgcuuuc ugggcucgcu ca                                                22
```

-continued

```
<210> SEQ ID NO 282
<211> LENGTH: 20
<212> TYPE: RNA
<213> ORGANISM: Homo sapiens

<400> SEQUENCE: 282
uggcugugug gcugcucugg                                                     20

<210> SEQ ID NO 283
<211> LENGTH: 18
<212> TYPE: RNA
<213> ORGANISM: Homo sapiens

<400> SEQUENCE: 283
caggcuggag ugcagugg                                                       18

<210> SEQ ID NO 284
<211> LENGTH: 22
<212> TYPE: RNA
<213> ORGANISM: Homo sapiens

<400> SEQUENCE: 284
ccgcuucgcu gcccuuccca ga                                                  22

<210> SEQ ID NO 285
<211> LENGTH: 22
<212> TYPE: RNA
<213> ORGANISM: Homo sapiens

<400> SEQUENCE: 285
uaauuucuga ugcucuuccc cu                                                  22

<210> SEQ ID NO 286
<211> LENGTH: 22
<212> TYPE: RNA
<213> ORGANISM: Homo sapiens

<400> SEQUENCE: 286
ugaggaggau cugaaggauu gg                                                  22

<210> SEQ ID NO 287
<211> LENGTH: 21
<212> TYPE: RNA
<213> ORGANISM: Homo sapiens

<400> SEQUENCE: 287
ugucccuagc caccccccagc a                                                  21

<210> SEQ ID NO 288
<211> LENGTH: 22
<212> TYPE: RNA
<213> ORGANISM: Homo sapiens

<400> SEQUENCE: 288
ucugcagccu accucaucag ac                                                  22

<210> SEQ ID NO 289
<211> LENGTH: 21
<212> TYPE: RNA
<213> ORGANISM: Homo sapiens

<400> SEQUENCE: 289
aaaguaauug ugguuuuugc a                                                   21
```

```
<210> SEQ ID NO 290
<211> LENGTH: 20
<212> TYPE: RNA
<213> ORGANISM: Homo sapiens

<400> SEQUENCE: 290
ugaggugacc gcagauggga                                              20

<210> SEQ ID NO 291
<211> LENGTH: 25
<212> TYPE: RNA
<213> ORGANISM: Homo sapiens

<400> SEQUENCE: 291
cucagugaug aaaacuuugu ccagu                                        25

<210> SEQ ID NO 292
<211> LENGTH: 22
<212> TYPE: RNA
<213> ORGANISM: Homo sapiens

<400> SEQUENCE: 292
aacucaggag gcagaacuug ca                                           22

<210> SEQ ID NO 293
<211> LENGTH: 22
<212> TYPE: RNA
<213> ORGANISM: Homo sapiens

<400> SEQUENCE: 293
auuuuuagua gagaugggu uu                                            22

<210> SEQ ID NO 294
<211> LENGTH: 21
<212> TYPE: RNA
<213> ORGANISM: Homo sapiens

<400> SEQUENCE: 294
aagugugggc ucuagaguug g                                            21

<210> SEQ ID NO 295
<211> LENGTH: 20
<212> TYPE: RNA
<213> ORGANISM: Homo sapiens

<400> SEQUENCE: 295
agggaacagc ugggugagcu                                              20

<210> SEQ ID NO 296
<211> LENGTH: 22
<212> TYPE: RNA
<213> ORGANISM: Homo sapiens

<400> SEQUENCE: 296
augggcagaa gggcagcuga ca                                           22

<210> SEQ ID NO 297
<211> LENGTH: 23
<212> TYPE: RNA
<213> ORGANISM: Homo sapiens

<400> SEQUENCE: 297
ugucagggcu ggacacagcu gca                                          23
```

-continued

```
<210> SEQ ID NO 298
<211> LENGTH: 24
<212> TYPE: RNA
<213> ORGANISM: Homo sapiens

<400> SEQUENCE: 298
cauccagggu ccucacugcc uguc                                           24

<210> SEQ ID NO 299
<211> LENGTH: 21
<212> TYPE: RNA
<213> ORGANISM: Homo sapiens

<400> SEQUENCE: 299
uugggguuug gggugcagac a                                              21

<210> SEQ ID NO 300
<211> LENGTH: 21
<212> TYPE: RNA
<213> ORGANISM: Homo sapiens

<400> SEQUENCE: 300
uaccccauau acaccucagc u                                              21

<210> SEQ ID NO 301
<211> LENGTH: 20
<212> TYPE: RNA
<213> ORGANISM: Homo sapiens

<400> SEQUENCE: 301
ucccuguccu ucuccaggcu                                                20

<210> SEQ ID NO 302
<211> LENGTH: 22
<212> TYPE: RNA
<213> ORGANISM: Homo sapiens

<400> SEQUENCE: 302
auuagguagu ggcaguggaa ca                                             22

<210> SEQ ID NO 303
<211> LENGTH: 21
<212> TYPE: RNA
<213> ORGANISM: Homo sapiens

<400> SEQUENCE: 303
gacaguaaca gcccgggaca g                                              21

<210> SEQ ID NO 304
<211> LENGTH: 20
<212> TYPE: RNA
<213> ORGANISM: Homo sapiens

<400> SEQUENCE: 304
aaaccuccac uuccuccuca                                                20

<210> SEQ ID NO 305
<211> LENGTH: 21
<212> TYPE: RNA
<213> ORGANISM: Homo sapiens

<400> SEQUENCE: 305
```

-continued cgaggcccca uggcgccgcc c                                                 21

<210> SEQ ID NO 306
<211> LENGTH: 22
<212> TYPE: RNA
<213> ORGANISM: Homo sapiens

<400> SEQUENCE: 306
agggccgguu cugagguuga gu                                                22

<210> SEQ ID NO 307
<211> LENGTH: 22
<212> TYPE: RNA
<213> ORGANISM: Homo sapiens

<400> SEQUENCE: 307
acgugcuggu cugugugcug gc                                                22

<210> SEQ ID NO 308
<211> LENGTH: 20
<212> TYPE: RNA
<213> ORGANISM: Homo sapiens

<400> SEQUENCE: 308
agggccgaag gguggaagcu                                                   20

<210> SEQ ID NO 309
<211> LENGTH: 21
<212> TYPE: RNA
<213> ORGANISM: Homo sapiens

<400> SEQUENCE: 309
ccaagagccu ggaacugcac c                                                 21

<210> SEQ ID NO 310
<211> LENGTH: 21
<212> TYPE: RNA
<213> ORGANISM: Homo sapiens

<400> SEQUENCE: 310
guuguagucc gugcgagaau a                                                 21

<210> SEQ ID NO 311
<211> LENGTH: 18
<212> TYPE: RNA
<213> ORGANISM: Homo sapiens

<400> SEQUENCE: 311
auugcacucc agccuggg                                                     18

<210> SEQ ID NO 312
<211> LENGTH: 26
<212> TYPE: RNA
<213> ORGANISM: Homo sapiens

<400> SEQUENCE: 312
cuauaguucc agcuacucag gaggcu                                            26

<210> SEQ ID NO 313
<211> LENGTH: 24
<212> TYPE: RNA
<213> ORGANISM: Homo sapiens

<400> SEQUENCE: 313

```
ugaucuccgc ucacugcaag cucg                                    24

<210> SEQ ID NO 314
<211> LENGTH: 21
<212> TYPE: RNA
<213> ORGANISM: Homo sapiens

<400> SEQUENCE: 314
ccaagucuua aucugucauc c                                       21

<210> SEQ ID NO 315
<211> LENGTH: 22
<212> TYPE: RNA
<213> ORGANISM: Homo sapiens

<400> SEQUENCE: 315
augcuggcgc uuucacacac uc                                      22

<210> SEQ ID NO 316
<211> LENGTH: 21
<212> TYPE: RNA
<213> ORGANISM: Homo sapiens

<400> SEQUENCE: 316
cacugcagua cugugcuggc a                                       21

<210> SEQ ID NO 317
<211> LENGTH: 22
<212> TYPE: RNA
<213> ORGANISM: Homo sapiens

<400> SEQUENCE: 317
aaaaaccacg aucacuuuug ca                                      22

<210> SEQ ID NO 318
<211> LENGTH: 20
<212> TYPE: RNA
<213> ORGANISM: Homo sapiens

<400> SEQUENCE: 318
ugauguccuc uguuccucag                                         20

<210> SEQ ID NO 319
<211> LENGTH: 22
<212> TYPE: RNA
<213> ORGANISM: Homo sapiens

<400> SEQUENCE: 319
cuggggaugg gaacuguugg ga                                      22

<210> SEQ ID NO 320
<211> LENGTH: 22
<212> TYPE: RNA
<213> ORGANISM: Homo sapiens

<400> SEQUENCE: 320
uugggauuga cgccacaugu cu                                      22

<210> SEQ ID NO 321
<211> LENGTH: 23
<212> TYPE: RNA
<213> ORGANISM: Homo sapiens
```

```
<400> SEQUENCE: 321
uccagacacu guggacugca gga                                              23

<210> SEQ ID NO 322
<211> LENGTH: 19
<212> TYPE: RNA
<213> ORGANISM: Homo sapiens

<400> SEQUENCE: 322
ccauggauau cuaggcucc                                                   19

<210> SEQ ID NO 323
<211> LENGTH: 22
<212> TYPE: RNA
<213> ORGANISM: Homo sapiens

<400> SEQUENCE: 323
ucgccaggcu ggaguguagu gg                                               22

<210> SEQ ID NO 324
<211> LENGTH: 19
<212> TYPE: RNA
<213> ORGANISM: Homo sapiens

<400> SEQUENCE: 324
acccagguug gagugcagu                                                   19

<210> SEQ ID NO 325
<211> LENGTH: 20
<212> TYPE: RNA
<213> ORGANISM: Homo sapiens

<400> SEQUENCE: 325
aggcuggagu gcaguggugc                                                  20

<210> SEQ ID NO 326
<211> LENGTH: 21
<212> TYPE: RNA
<213> ORGANISM: Homo sapiens

<400> SEQUENCE: 326
cgcugacccg ccuucuccgc a                                                21

<210> SEQ ID NO 327
<211> LENGTH: 21
<212> TYPE: RNA
<213> ORGANISM: Homo sapiens

<400> SEQUENCE: 327
ccuggcaaua cacaucuacu g                                                21

<210> SEQ ID NO 328
<211> LENGTH: 20
<212> TYPE: RNA
<213> ORGANISM: Homo sapiens

<400> SEQUENCE: 328
cuuguugaug ugcugcgccu                                                  20

<210> SEQ ID NO 329
<211> LENGTH: 19
<212> TYPE: RNA
<213> ORGANISM: Homo sapiens
```

```
<400> SEQUENCE: 329
cccggguuca agugauucu                                            19

<210> SEQ ID NO 330
<211> LENGTH: 23
<212> TYPE: RNA
<213> ORGANISM: Homo sapiens

<400> SEQUENCE: 330
ucagggcgaa gcuuauccau ugc                                       23

<210> SEQ ID NO 331
<211> LENGTH: 22
<212> TYPE: RNA
<213> ORGANISM: Homo sapiens

<400> SEQUENCE: 331
aaggcucaaa cuccugaacu ca                                        22

<210> SEQ ID NO 332
<211> LENGTH: 22
<212> TYPE: RNA
<213> ORGANISM: Homo sapiens

<400> SEQUENCE: 332
ucccagguuc aagcaauucu cc                                        22

<210> SEQ ID NO 333
<211> LENGTH: 19
<212> TYPE: RNA
<213> ORGANISM: Homo sapiens

<400> SEQUENCE: 333
ucccugcaac cuagagcuc                                            19

<210> SEQ ID NO 334
<211> LENGTH: 21
<212> TYPE: RNA
<213> ORGANISM: Homo sapiens

<400> SEQUENCE: 334
cccaggcugg aaugcaaugg c                                         21

<210> SEQ ID NO 335
<211> LENGTH: 24
<212> TYPE: RNA
<213> ORGANISM: Homo sapiens

<400> SEQUENCE: 335
gccccagagc cggaggcugc agug                                      24

<210> SEQ ID NO 336
<211> LENGTH: 23
<212> TYPE: RNA
<213> ORGANISM: Homo sapiens

<400> SEQUENCE: 336
cuggagagaa aggcagucag agg                                       23

<210> SEQ ID NO 337
<211> LENGTH: 22
<212> TYPE: RNA
```

-continued

```
<213> ORGANISM: Homo sapiens

<400> SEQUENCE: 337
ugcgggcccu gggaguggag ac                                        22

<210> SEQ ID NO 338
<211> LENGTH: 26
<212> TYPE: RNA
<213> ORGANISM: Homo sapiens

<400> SEQUENCE: 338
cauugaugau cguucuucuc uccgua                                    26

<210> SEQ ID NO 339
<211> LENGTH: 20
<212> TYPE: RNA
<213> ORGANISM: Homo sapiens

<400> SEQUENCE: 339
uuucacugau gugcuccacu                                           20

<210> SEQ ID NO 340
<211> LENGTH: 19
<212> TYPE: RNA
<213> ORGANISM: Homo sapiens

<400> SEQUENCE: 340
caauccuccc accucggcc                                            19

<210> SEQ ID NO 341
<211> LENGTH: 23
<212> TYPE: RNA
<213> ORGANISM: Homo sapiens

<400> SEQUENCE: 341
ugucuagaca aggcugggga aau                                       23

<210> SEQ ID NO 342
<211> LENGTH: 21
<212> TYPE: RNA
<213> ORGANISM: Homo sapiens

<400> SEQUENCE: 342
acggcgugac acaucuucug u                                         21

<210> SEQ ID NO 343
<211> LENGTH: 24
<212> TYPE: RNA
<213> ORGANISM: Homo sapiens

<400> SEQUENCE: 343
ugcccgugag cuccaccugc cugc                                      24

<210> SEQ ID NO 344
<211> LENGTH: 21
<212> TYPE: RNA
<213> ORGANISM: Homo sapiens

<400> SEQUENCE: 344
ugggugacag agugagaccc c                                         21

<210> SEQ ID NO 345
<211> LENGTH: 20
```

```
<212> TYPE: RNA
<213> ORGANISM: Homo sapiens

<400> SEQUENCE: 345
auuggcacug cacaugauug                                                  20

<210> SEQ ID NO 346
<211> LENGTH: 21
<212> TYPE: RNA
<213> ORGANISM: Homo sapiens

<400> SEQUENCE: 346
cacugcacuc cagcuuggau g                                                21

<210> SEQ ID NO 347
<211> LENGTH: 21
<212> TYPE: RNA
<213> ORGANISM: Homo sapiens

<400> SEQUENCE: 347
gcuccacuuu caguucucuu g                                                21

<210> SEQ ID NO 348
<211> LENGTH: 22
<212> TYPE: RNA
<213> ORGANISM: Homo sapiens

<400> SEQUENCE: 348
agcccaggag gucgggacug ca                                               22

<210> SEQ ID NO 349
<211> LENGTH: 23
<212> TYPE: RNA
<213> ORGANISM: Homo sapiens

<400> SEQUENCE: 349
aggagugggg ggugggacgu aag                                              23

<210> SEQ ID NO 350
<211> LENGTH: 21
<212> TYPE: RNA
<213> ORGANISM: Homo sapiens

<400> SEQUENCE: 350
agagaacuaa aacuggaguc u                                                21

<210> SEQ ID NO 351
<211> LENGTH: 23
<212> TYPE: RNA
<213> ORGANISM: Homo sapiens

<400> SEQUENCE: 351
ccagagcagc cugcgguaac agu                                              23

<210> SEQ ID NO 352
<211> LENGTH: 22
<212> TYPE: RNA
<213> ORGANISM: Homo sapiens

<400> SEQUENCE: 352
ucccagguuc aagcaauucu uc                                               22

<210> SEQ ID NO 353
```

```
<211> LENGTH: 18
<212> TYPE: RNA
<213> ORGANISM: Homo sapiens

<400> SEQUENCE: 353
gcuuacgccu guaauccc                                                    18

<210> SEQ ID NO 354
<211> LENGTH: 21
<212> TYPE: RNA
<213> ORGANISM: Homo sapiens

<400> SEQUENCE: 354
gcugcguuuc auggagcccc u                                                21

<210> SEQ ID NO 355
<211> LENGTH: 21
<212> TYPE: RNA
<213> ORGANISM: Homo sapiens

<400> SEQUENCE: 355
guggucuaag gcgcuggauu u                                                21

<210> SEQ ID NO 356
<211> LENGTH: 20
<212> TYPE: RNA
<213> ORGANISM: Homo sapiens

<400> SEQUENCE: 356
accuucaacc ucccgggcuc                                                  20

<210> SEQ ID NO 357
<211> LENGTH: 21
<212> TYPE: RNA
<213> ORGANISM: Homo sapiens

<400> SEQUENCE: 357
aggccauucc ccaucagaug a                                                21

<210> SEQ ID NO 358
<211> LENGTH: 21
<212> TYPE: RNA
<213> ORGANISM: Homo sapiens

<400> SEQUENCE: 358
ucagcugaaa caguccugga c                                                21

<210> SEQ ID NO 359
<211> LENGTH: 21
<212> TYPE: RNA
<213> ORGANISM: Homo sapiens

<400> SEQUENCE: 359
uuccccgcuu cccccuagg g                                                 21

<210> SEQ ID NO 360
<211> LENGTH: 19
<212> TYPE: RNA
<213> ORGANISM: Homo sapiens

<400> SEQUENCE: 360
ucacuaaagu ugguauaca                                                   19
```

```
<210> SEQ ID NO 361
<211> LENGTH: 22
<212> TYPE: RNA
<213> ORGANISM: Homo sapiens

<400> SEQUENCE: 361
uggagguugc agugagcuga ga                                                  22

<210> SEQ ID NO 362
<211> LENGTH: 22
<212> TYPE: RNA
<213> ORGANISM: Homo sapiens

<400> SEQUENCE: 362
gaugggaucg gagcucuaga gu                                                  22

<210> SEQ ID NO 363
<211> LENGTH: 24
<212> TYPE: RNA
<213> ORGANISM: Homo sapiens

<400> SEQUENCE: 363
cccggggguc gagacugcag ugag                                                24

<210> SEQ ID NO 364
<211> LENGTH: 21
<212> TYPE: RNA
<213> ORGANISM: Homo sapiens

<400> SEQUENCE: 364
caccuggguu guccccucua g                                                   21

<210> SEQ ID NO 365
<211> LENGTH: 21
<212> TYPE: RNA
<213> ORGANISM: Homo sapiens

<400> SEQUENCE: 365
cugcagugag cugagauugu g                                                   21
```